United States Patent
Sasaki et al.

(10) Patent No.: US 6,306,862 B1
(45) Date of Patent: *Oct. 23, 2001

(54) TRITERPENE DERIVATIVES AND PHARMACEUTICALS FOR TREATING HEPATIC DISORDERS

(75) Inventors: Kazue Sasaki; Nobuto Minowa; Shoji Nishiyama; Hiroyuki Kuzuhara, all of Kanagawa-ken (JP)

(73) Assignee: Meiji Seika Kaisha, Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/983,127

(22) PCT Filed: Jul. 8, 1996

(86) PCT No.: PCT/JP96/01891

§ 371 Date: Jun. 1, 1998

§ 102(e) Date: Jun. 1, 1998

(87) PCT Pub. No.: WO97/03088

PCT Pub. Date: Jan. 30, 1997

(30) Foreign Application Priority Data

Jul. 7, 1995 (JP) .................................................. 7-171900
Feb. 26, 1996 (JP) .................................................. 8-037830

(51) Int. Cl.$^7$ .................................................. A61K 31/495
(52) U.S. Cl. .......................... 514/255; 424/49; 549/200; 552/261; 560/116; 568/579
(58) Field of Search .............................. 552/261; 424/49; 514/255; 568/579; 549/200; 560/116

(56) References Cited

U.S. PATENT DOCUMENTS

| | | | |
|---|---|---|---|
| 4,524,067 | 6/1985 | Arichi et al. | 514/33 |
| 4,606,911 | * 8/1986 | Hayashi et al. | 424/49 |
| 4,871,740 | * 10/1989 | Kurono et al. | 514/255 |

FOREIGN PATENT DOCUMENTS

| | | |
|---|---|---|
| 61-37749 | 2/1986 | (JP) . |
| 61-85344 | 4/1986 | (JP) . |
| 62-126149 | 6/1987 | (JP) . |

OTHER PUBLICATIONS

Hjiroji Ohminami et al., "Effect of Soyasaponins on Liver Injury by Highly Peroxidized Fat in Rats", Planta Medica De Thieme, Stuttgart, vol. 6 (6), pp. 440–441 (1984).

Junei Kinjo et al., "Triterpene Saponins from *Vigna unguciculata, Phaseolus vulgaris, Phaseolus coccineous, Canavalia gladiata,* and *Lupinus polyphyllus x arboreus*: Their Structures, Antithepatotoxic Activities, and Antioxidative Inactivity", Food Factors for Cancer Prevention, pp. 323–327 (1995).

* cited by examiner

Primary Examiner—Paul J. Killos
Assistant Examiner—Taylor V. Oh
(74) *Attorney, Agent, or Firm*—Wenderoth, Lind & Ponack, L.L.P.

(57) ABSTRACT

A pharmaceutical composition for treating a hepatic disorder, comprising a triterpene derivative represented by the formula (I) or a pharmaceutically acceptable salt thereof is disclosed:

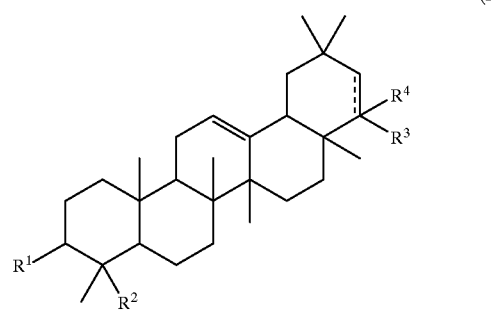

(I)

wherein $R^1$ represents a hydroxyl group, alkoxy, alkylcarbonyloxy, or aralkyloxy; $R^2$ represents alkyl, —$CH_2OR^5$, wherein $R^5$ represents a hydrogen atom, alkyl, aralkyl, or alkylcarbonyl, formyl, —$COOR^6$, wherein $R^6$ represents a hydrogen atom or alkyl, or —$CH_2N(R^7)R^8$; or $R^1$ and $R^2$ combine with each other to form —O—$CR^9(R^{10})$—$OCH_2$—, wherein $R^9$ and $R^{10}$, which may be the same or different, represent a hydrogen atom, alkyl, or aryl; $R^3$ and $R^4$, which may be the same or different, represent a hydrogen atom, a hydroxyl group, alkyl, hydroxyalkyl, formyl, —$COOR^{11}$, wherein $R^{11}$ represents a hydrogen atom or alkyl, or —$OR^{12}$, wherein $R^{12}$ represents alkyl, aralkyl, $C_{1-6}$ alkylcarbonyl, arylcarbonyl, alkenyl, alkenylcarbonyl, or arylalkenylcarbonyl which may be optionally substituted; or $R^3$ and $R^4$ combine with each other to form a methylene group; and ⎯ ⎯ ⎯ represents a single or double bond, provided that, when ⎯ ⎯ ⎯ represents a double bond, $R^4$ is absent.

41 Claims, No Drawings

TRITERPENE DERIVATIVES AND PHARMACEUTICALS FOR TREATING HEPATIC DISORDERS

BACKGROUND OF THE INVENTION

1. Field of Invention

The present invention relates to triterpene derivatives usable as therapeutic agents for hepatic disorders.

2. Description of the Related Art

A liver is an important organ which has various functions necessary for maintaining life of a living body, such as detoxication, various metabolisms, and storage of substances. It, however, often undergoes acute or chronic damage due to viruses, drugs, alcohols and other various causes. This induces viral hepatitis, drug-induced hepatopathy, alcoholic hepatopathy, fatty liver, and, in addition, diseases such as cirrhosis and hepatic cancer.

For treating such disorders, alimentary therapy, rest cure, and other therapies using glycyrrhizin preparations, adrenocortical steroids, interferons and the like have hitherto been employed. These therapies, however, may not be satisfactorily effective for the treatment of the hepatic disorders. Glycyrrhizin and interferon are intravenously administered and, hence, unsuitable for prolonged administration. Further, the interferon and steroids have a problem of side effect.

Some triterpene derivatives have anticomplementary activity and platelet aggregation inhibitory activity. Thus, they are known as prophylactic and therapeutic agents for immunological diseases and thrombosis (Japanese Patent Laid-Open No. 85344/1986). Further, triterpene derivatives are disclosed, for example, in Japanese Patent Laid-Open No. 37749/1986, Chem. Pharm. Bull., 36, 153 (1988), Chem. Pharm. Bull., 24, 121 (1976), Chem. Pharm. Bull., 30, 2294 (1982), Chem. Pharm. Bull., 33, 4267 (1985), Chem. Pharm. Bull., 31, 664 (1983), Chem. Pharm. Bull., 31, 674 (1983), Phytochemistry 27, 3563 (1988), Planta Medica 46, 52 (1982), J. Chem. Soc., and Chem. Comm., 785 (1982).

However, so far as the present inventors know, there is no report which discloses that the triterpene derivatives are effective as a therapeutic agent for treating hepatic disorders.

SUMMARY OF THE INVENTION

The present inventors have now found that triterpene derivatives are effective for treating hepatic disorders. Further, they have succeeded in synthesis of novel triterpene derivatives. The present invention is based on such novel finding.

Thus, according to one aspect of the present invention, there is provided a therapeutic agent for a hepatic disorder, comprising a triterpene derivative represented by the formula (I) or a pharmaceutically acceptable salt thereof:

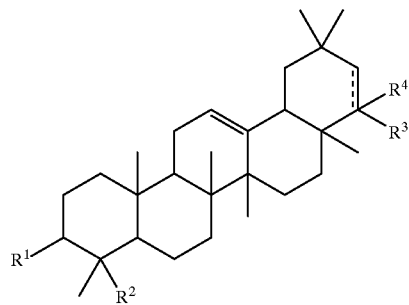

(I)

wherein $R^1$ represents a hydroxyl group,
  $C_{1-6}$ alkoxy,
  $C_{1-6}$ alkylcarbonyloxy, or aralkyloxy which may be optionally substituted;

$R^2$ represents $C_{1-6}$ alkyl,
  —$CH_2OR^5$ wherein $R^5$ represents a hydrogen atom, $C_{1-6}$ alkyl, aralkyl which may be optionally substituted, or $C_{1-6}$ alkylcarbonyl,
  formyl,
  —$COOR^6$ wherein $R^6$ represents a hydrogen atom or $C_{1-6}$ alkyl), or
  —$CH_2N(R^7)R^8$ wherein $R^7$ and $R^8$, which may be the same or different, represent a hydrogen atom or $C_{1-6}$ alkyl; or $R^1$ and $R^2$ may combine with each other to form —O—$CR^9(R^{10})$—$OCH_2$— wherein $R^9$ and $R^{10}$, which may be the same or different, represent a hydrogen atom, $C_{1-6}$ alkyl, or aryl;

$R^3$ and $R^4$, which may be the same or different, represent
  a hydrogen atom,
  a hydroxyl group,
  $C_{1-6}$ alkyl,
  hydroxy $C_{1-6}$ alkyl,
  formyl,
  —$COOR^{11}$ wherein $R^{11}$ represents a hydrogen atom or $C_{1-6}$ alkyl, or
  —$OR^{12}$ wherein $R^{12}$ represents $C_{1-6}$ alkyl, aralkyl which may be optionally substituted, $C_{1-6}$ alkylcarbonyl, arylcarbonyl which may be optionally substituted, $C_{2-6}$ alkenyl, $C_{2-6}$ alkenylcarbonyl, or arylalkenylcarbonyl which may be optionally substituted; or $R^3$ and $R^4$ combine with each other to form a methylene group;

═ ═ ═ represents a single or double bond, provided that, when ═ ═ ═ represents a double bond, $R^4$ is absent.

The novel triterpene derivative according to another aspect of the present invention is represented by the formula (II) or a pharmaceutically acceptable salt thereof:

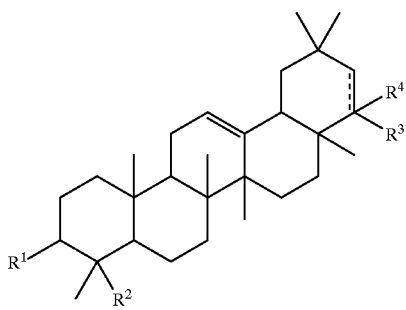

(II)

wherein
R¹ represents a hydroxyl group,
$C_{1-6}$ alkoxy,
$C_{1-6}$ alkylcarbonyloxy, or
aralkyloxy which may be optionally substituted;
R² represents $C_{1-6}$ alkyl,
—CH₂OR⁵ wherein R⁵ represents a hydrogen atom, $C_{1-6}$ alkyl, aralkyl which may be optionally substituted, or $C_{1-6}$ alkylcarbonyl,
formyl,
—COOR⁶ wherein R⁶ represents a hydrogen atom or $C_{1-6}$ alkyl), or
—CH₂N(R⁷)R⁸ wherein R⁷ and R⁸, which may be the same or different, represent a hydrogen atom or $C_{1-6}$ alkyl; or
R¹ and R² may combine with each other to form —O—CR⁹(R¹⁰)—OCH₂— wherein R⁹ and R¹⁰, which may be the same or different, represent a hydrogen atom, a $C_{1-6}$ alkyl group, or aryl which may be optionally substituted;
R³ and R⁴, which may be the same or different, represent $C_{1-6}$ alkyl,
hydroxy $C_{1-6}$ alkyl,
formyl,
—COOR¹¹ wherein R¹¹ represents a hydrogen atom or $C_{1-6}$ alkyl, or
—OR¹² wherein R¹² represents $C_{1-6}$ alkyl, aralkyl which may be optionally substituted, arylcarbonyl which may be optionally substituted, $C_{2-6}$ alkenyl, $C_{2-6}$ alkenylcarbonyl, or arylalkenylcarbonyl which may be optionally substituted; or
R³ and R⁴ may combine with each other to form a methylene group;

═ ═ ═ represents a single or double bond, provided that, when ═ ═ ═ represents a double bond, R⁴ is absent;
when R¹ and R² may combine with each other to form —O—CR⁹(R¹⁰)—OCH₂— wherein any one of R⁹ and R¹⁰ represents aryl, R³ and R⁴ may further represent a hydrogen atom, a hydroxyl group, or aralkyloxy;
when any one of R³ and R⁴ represents a $C_{1-6}$ alkyl group, the other may further represent a hydroxyl group; and
when R² represents —CH₂OR⁵, R³ and R⁴ may further represent a hydrogen atom.
Further, novel compounds provided by the present invention are:
a compound represented by the formula (II) wherein R¹ represents a hydroxyl group, R² represents —COO— $C_{1-6}$alkyl, R³ represents a hydrogen atom and R⁴ represents a hydroxyl group;

a compound represented by the formula (II) wherein R¹ represents $C_{1-6}$ alkoxy, R² represents —CH₂OH, R³ represents a hydrogen atom and R⁴ represents a hydroxyl group,
a compound represented by the formula (II) wherein R¹ represents aralkyloxy, R² represents formyl, carboxyl, —COO—$C_{1-6}$ alkyl, or —CH₂OR⁵, wherein R⁵ represents a hydrogen atom, $C_{1-6}$ alkyl, or $C_{1-6}$ alkylcarbonyl, R³ represents a hydrogen atom and R⁴ represents aralkyloxy which may be optionally substituted; and
a compound represented by the formula (II) wherein R¹ represents a hydroxyl group or $C_{1-6}$ alkoxy, R² represents aralkyloxymethyl which may be optionally substituted, R³ represents a hydrogen atom and R⁴ represents aralkyloxy which may be optionally substituted.

DESCRIPTION OF THE PREFERRED EMBODIMENTS

Therapeutic Agent for Hepatic Disorders/Compounds of Formula (I)

The compounds represented by the formula (I) and salts thereof are effective for the treatment of hepatic disorders. Hepatic disorders, to which the compounds represented by the formula (I) can be applied, include acute and chronic viral hepatitis, and drug-induced, toxic, alcoholic, intrahepatic cholestasis, and inborn metabolic error hepatopathy. The term "hepatopathy" used herein refers to inflammatory diseases and, depending upon the progress of symptom, is used as a term include also fatty liver, cirrhosis, and hepatoma.

Specifically, the triterpene derivatives represented by the formula (I), when incubated together with human hepatoma cells (Hep G2) in the presence of aflatoxin $B_1$ (hepatopathy-inducing substance), has an inhibitory activity against necrosis of such cells.

As used herein, the term "alkyl" as a group or a part of a group means both straight and branched chain alkyls.

Specific examples of this group include methyl, ethyl, propyl, iso-propyl, n-butyl, iso-butyl, and t-butyl. The term "halogen atom" means a fluorine, chlorine, bromine, or iodine atom. The term "aryl" as a group or a part of a group preferably means phenyl, naphthyl, tolyl, methoxyphenyl or the like. The term "aralkyl" as a group or a part of a group preferably means phenyl $C_{1-4}$ alkyl, more preferably benzyl, phenethyl or the like. One or more hydrogen atoms, preferably one or two hydrogen atoms, on the "aryl" or "aralkyl" may be optionally substituted, and examples of the substituent include a hydroxyl group, $C_{1-6}$ alkoxy (preferably $C_{1-4}$ alkoxy, more preferably methoxy), a halogen atom, amino, dimethylamino, acetoxy, methylenedioxy, and nitro. Examples of substituted aryl and aralkyl include methoxy, phenyl, hydroxyphenyl, dihydroxyphenyl, and dimethoxyphenyl.

In the formula (I), the $C_{1-6}$ alkoxy represented by R¹ is preferably $C_{1-4}$ alkoxy, more preferably methoxy or ethoxy. Specific examples thereof include methoxy, ethoxy, propyloxy, butyloxy, pentyloxy, and hexyloxy. The $C_{1-6}$ alkylcarbonyl is preferably $C_{1-4}$ alkylcarbonyl, and specific examples thereof include acetyl, propionyl, butyryl, pentanoyl, and hexanoyl. The aralkyloxy represented by R¹ is preferably benzyloxy, phenetyloxy, methylbenzyloxy, and naphthylmethyloxy.

In the formula (I), —CH₂OR⁵ represented by R² is preferably —CH₂OH, —CH₂O—$C_{1-4}$ alkyl, —CH₂O—(phenyl $C_{1-4}$ alkyl), or —CH₂O—CO—$C_{1-4}$ alkyl, more preferably hydroxymethyl. The group —COOR$^6$ represented by R$^2$ is preferably —COO—C$_{1-6}$ alkyl or COOH.

Further, in the formula (I), R$^1$ and R$^2$ may combine with each other to form —O—CR$^9$(R$^{10}$)—OCH$_2$— wherein R$^9$ and R$^{10}$, which may be the same or different, represent a hydrogen atom, C$_{1-6}$ alkyl, or aryl. Preferred examples thereof include —O—CR$^9$(R$^{10}$)—OCH$_2$— wherein both R$^9$ and R$^{10}$ represent C$_{1-6}$ alkyl, preferably C$_{1-4}$ alkyl, more preferably methyl or ethyl and —O—CR$^9$(R$^{10}$)—OCH$_2$— wherein any one of R$^9$ and R$^{10}$ represent a hydrogen atom with the other representing aryl, preferably phenyl, tolyl, xylyl, biphenyl, naphthyl, anthryl, or phenanthryl.

In the formula (I), the C$_{1-6}$ alkyl represented by R$^3$ R$^4$ is preferably C$_{1-4}$ alkyl, more preferably methyl or ethyl. The hydroxy C$_{1-6}$ alkyl represented by R$^3$ and R$^4$ is preferably hydroxy C$_{1-4}$ alkyl, more preferably hydroxymethyl.

In the formula (I), —COOR$^{11}$ represented by R$^3$ or R$^4$ is preferably —COOH or —COO—C$_{1-4}$ alkyl.

Further, in the formula (I), R$^{12}$ in —OR$^{12}$ represented by R$^3$ or R$^4$ represents C$_{1-6}$ alkyl, aralkyl, C$_{1-6}$ alkylcarbonyl, arylcarbonyl, C$_{2-6}$ alkenyl, C$_{2-6}$ alkenylcarbonyl, or arylalkenylcarbonyl. Further, the C$_{2-6}$ alkenyl is preferably C$_{2-4}$ alkenyl, and specific examples thereof include vinyl, propenyl, allyl, butenyl, 2-methylpropenyl, pentenyl, and hexenyl. Examples of the aralkyl include benzyl, phenethyl, methylbenzyl, naphthylmethyl, and phenylpropyl. The C$_{1-6}$ alkylcarbonyl is preferably C$_{1-4}$ alkylcarbonyl, and specific examples thereof include acetyl, propionyl, butyryl, pentanoyl, and hexanoyl. Preferred examples of arylcarbonyls include benzoyl and naphthylcarbonyl. The C$_{2-6}$ alkenyl is preferably C$_{2-4}$ alkenylcarbonyl, and specific examples thereof include acryloyl, allylcarbonyl, and butenoyl. The C$_{2-6}$ alkenylcarbonyl is preferably C$_{2-4}$ alkenylcarbonyl. Specific examples of the arylalkenylcarbonyl include cinnamoyl and phenylbutenoyl.

R$^3$ and R$^4$ may combine with each other to form a methylene group.

In the formula (I), — — — represents a single bond or a double bond.

When — — — represents a double bond, preferably, R$^1$ represents a hydrogen atom with R$^2$ representing —CH$_2$OH, or R$^1$ and R$^2$ combine with each other to form —O—CR$^9$(R$^{10}$)—OCH$_2$—, wherein R$^9$ and R$^{10}$ are as defined above, and R$^3$ represents a hydrogen atom.

The compounds represented by the formula (I) have isomers, and the present invention embraces such isomers and mixtures thereof.

According to a preferred embodiment of the present invention, preferred compounds have a configuration represented by the following formula (I-1):

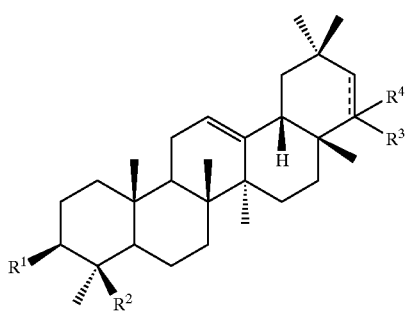

(I-1)

Further, the compounds represented by the formula (I) can easily form a salt with a pharmaceutically acceptable base. Preferred bases include inorganic bases, such as sodium hydroxide, potassium hydroxide, aluminum hydroxide, sodium carbonate, potassium carbonate, and sodium hydrogencarbonate, and organic bases, such as piperazine, morpholine, piperidine, ethylamine, and trimethylamine.

Preferred compounds, of the present invention, represented by the formula (I) include:

a group of compounds wherein R$^1$ represents a hydroxyl group, R$^2$ represents —CH$_2$OR$^5$ and R$^3$ represents a hydrogen atom, amoung them, more preferably a group of compounds wherein R$^4$ represents a hydroxyl group or —OR$^{12}$ and a group of compounds wherein R$^1$ represents C$_{1-6}$ alkoxy, a group of compounds wherein R$^1$ represents a hydroxyl group, R$^2$ represents formyl, R$^3$ represents a hydrogen atom and R$^4$ represents a hydroxyl group, a group of compounds wherein R$^1$ represents a hydroxyl group or aralkyloxy, R$^2$ represents —COOR$^6$, R$^3$ represents a hydrogen atom and R$^4$ represents a hydroxyl group or —OR$^{12}$, a group of compounds wherein R$^1$ represents a hydroxyl group, C$_{1-6}$ alkoxy, or C$_{1-6}$ alkylcarbonyloxy, R$^2$ represents —CH$_2$OR$^5$, and R$^3$ and R$^4$ represent a hydrogen atom, a group of compounds wherein R$^1$ represents a hydroxyl group, R$^2$ represents —CH$_2$OR$^5$, R$^3$ represents C$_{1-6}$ alkyl, and R$^4$ represents a hydroxyl group, and a group of compounds wherein R$^1$ represents a hydroxyl group, R$^2$ represents —CH$_2$OR$^5$, R$^3$ represents a hydrogen atom and R$^4$ represents hydroxy C$_{1-6}$ alkyl or carboxyl.

Although the compound represented by the formula (I) may be administered as a raw material, it may be preferably administered as a pharmaceutical composition. A pharmaceutical composition, as a therapeutic agent for hepatic disorders, comprising as an active ingredient the compound of the formula (I) or a salt thereof can be administered either orally or parenterally (e.g., intravenous injection, intramuscular injection, subcutaneous administration, rectal administration, percutaneous administration) to humans or animals other than humans.

Therefore, the therapeutic agent for hepatic disorders according to the present invention may be made into a formulation suitable for the route of administration. Specifically, it may be made into any of the following preparations: an injection such as intravenous or intramuscular injection; an oral preparation such as a capsule, a tablet, a granule, a powder, a pill, fine subtilaes, or a troche; a preparation for rectal administration; an oleaginous suppository; and an aqueous suppository. The above-described various preparations can be prepared by a conventional method using an excipient, a filler, a binder, a wetting agent, a disintegrating agent, a surface active agent, a lubricant, a dispersing agent, a buffer, a preservative, a solubilizer, an antiseptic, a flavor, a soothing agent, a stabilizer and the like. Examples of the above additives which are nontoxic and employable in the preparations include milk sugar, fruit sugar, grape sugar, starch, gelatin, magnesium carbonate, synthetic magnesium silicate, talc, magnesium stearate, methyl cellulose, carboxymethyl cellulose or a salt thereof, gum arabic, polyethylene glycol, syrup, vaseline, glycerin, ethanol, propylene glycol, citric acid, sodium chloride, sodium sulfite and sodium phosphate.

The dosage of the compound represented by the formula (I) may vary depending upon the age, weight, conditions, or severity of the disease of a patient. In general, however, it is approximately 0.1 to 1000 mg, preferably 1 to 100 mg per day for adult human, once or twice a day. The administration may be made either orally or parenterally.

Novel triterpene derivatives/compounds of formula (II)

According to another aspect of the present invention, novel triterpene derivatives are provided. The novel triterpene derivatives of the present invention are compounds represented by the formula (II).

In the formula (II), when $R^1$, $R^2$, $R^3$, and $R^4$ are as defined above in the formula (I), preferred compounds represented by the formula (II) may be the same as those described above in the formula (I).

The compounds represented by the formula (II) also have isomers, and the present invention embraces these isomers and mixtures thereof.

According to a preferred embodiment of the present invention, preferred compounds have a configuration represented by the following formula (II-1):

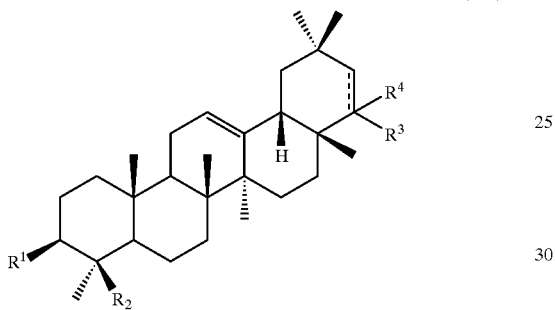

(II-1)

Further, the compounds represented by the formula (II) can easily form a salt with a pharmaceutically acceptable base. Preferred bases include those exemplified above in the formula (I).

According to a preferred embodiment of the present invention, preferred compounds, of the present invention, represented by the formula (II) include:

- a group of compounds wherein $R^1$ represents a hydroxyl group, $R^2$ represents —CH$_2$OR$^5$ and $R^3$ represents a hydrogen atom, particularly a group of compounds wherein $R^5$ represents a hydrogen atom and $R^4$ represents —OR$^{12}$ wherein $R^{12}$ represents $C_{1-6}$ alkyl, aralkyl, arylcarbonyl, $C_{2-6}$ alkenyl, $C_{2-6}$ alkenylcarbonyl, or arylalkenylcarbonyl,
- a group of compounds wherein $R^1$ and $R^2$ combine with each other to form —O—CR$^9$(R$^{10}$)—OCH$_2$, particularly a group of compounds wherein $R^9$ and $R^{10}$ represent methyl, $R^3$ represents a hydrogen atom and $R^4$ represents —OR$^{12}$ wherein $R^{12}$ represents $C_{1-6}$ alkyl, aralkyl, arylcarbonyl, $C_{2-6}$ alkenyl, $C_{2-6}$ alkenylcarbonyl, or arylalkenylcarbonyl, a group of compounds wherein $R^9$ represents a hydrogen atom and $R^{10}$ represents aryl, and a group of compounds wherein $R^3$ and $R^4$ represent a hydrogen atom, or $R^3$ represents a hydrogen atom with $R^4$ representing a hydroxyl group or aralkyloxy,
- a group of compounds wherein $R^1$ represents a hydroxyl group or aralkyloxy (preferably phenyl $C_{1-4}$ alkyl), $R^2$ represents —CH$_2$OR$^5$ and both $R^3$ and $R^4$ represent a hydrogen atom,
- a group of compounds wherein $R^1$ represents a hydroxyl group, $C_1$ alkoxy or $C_{1-6}$ alkylcarbonyloxy, $R^2$ represents —CH$_2$OR$^5$ (wherein $R^5$ preferably represents a hydrogen atom or aralkyl, more preferably phenyl $C_{1-4}$ alkyl) and $R^3$ and $R^4$ represent a hydrogen atom,
- a group of compounds wherein $R^1$ represents a hydroxyl group, $R^2$ represents —CH$_2$OR$^5$ (preferably $R^5$=H), $R^3$ represents $C_{1-6}$ alkyl and $R_4$ represent a hydroxyl group,
- a group of compounds wherein $R^1$ represents a hydroxyl group, $R^2$ represents —CH$_2$OR$^5$ (preferably $R^5$=H), $R^3$ represents a hydrogen atom and $R^4$ represents hydroxy $C_{1-6}$ alkyl or —COOR$^{11}$ (preferably $R^{11}$=H).
- a group of compounds wherein $R^1$ represents optionally substituted aralkyloxy (preferably phenyl $C_{1-4}$ alkyloxy), $R^2$ represents —CH$_2$OR$^5$, wherein $R^5$ represents a hydrogen atom, $C_{1-6}$ alkyl (preferably $C_{1-4}$ alkyl), or $C_{1-6}$ alkylcarbonyl (preferably $C_{1-4}$ alkylcarbonyl), and $R^3$ and $R^4$ represent a hydrogen atom,
- a group of compounds wherein $R^1$ represents a hydroxyl group, $R^2$ represents —CH$_2$OR$^5$, wherein $R^5$ represents $C_{1-6}$ alkyl (preferably $C_{1-4}$ alkyl) or $C_{1-6}$ alkylcarbonyl (preferably $C_{1-4}$ alkylcarbonyl), and $R^3$ and $R^4$ represent a hydrogen atom,
- a group of compounds wherein $R^1$ represents a hydroxyl group, $C_{1-6}$ alkoxy (preferably $C_{1-4}$ alkoxy), or $C_{1-6}$ alkylcarbonyloxy (preferably $C_{1-4}$ alkylcarbonyloxy), $R^2$ represents —CH$_2$OR$^5$, wherein $R^5$ represents optionally substituted aralkyl (preferably phenyl $C_{1-4}$ alkyl), and $R^3$ and $R^4$ represent a hydrogen atom,
- a group of compounds wherein $R^1$ represents $C_{1-6}$ alkoxy (preferably $C_{1-4}$ alkoxy) or $C_{1-6}$ alkylcarbonyloxy (preferably $C_{1-4}$ alkylcarbonyloxy), $R^2$ represents —CH$_2$OH and $R^3$ and $R^4$ represent a hydrogen atom,
- a group of compounds wherein $R^1$ represents a hydroxyl group, $R^2$ represents —CH$_2$OR$^5$ (preferably $R^5$=H) and $R^3$ and $R^4$ combine with each other to form a methylene group, and
- a group of compounds wherein $R^1$ and $R^2$ combine with each other to form —O—CR$^9$(R$^{10}$)—OCH$_2$— (preferably $R^9$=$R^{10}$=methyl) and ≡≡≡ represents a double bond.

Further novel compounds, of the present invention, represented by the formula (II) are:

- a compound wherein $R^1$ represents a hydroxyl group, $R^2$ represents —COO—$C_{1-6}$ alkyl (preferably —COO—$C_{1-4}$ alkyl), $R^3$ represents a hydrogen atom and $R^4$ represents a hydroxyl group,
- a compound wherein $R^1$ represents $C_{1-6}$ alkoxy (preferably $C_{1-4}$ alkyl), $R^2$ represents —CH$_2$OH, $R^3$ represents a hydrogen atom and $R^4$ represents a hydroxyl group,
- a compound wherein $R^1$ represents aralkyloxy (preferably phenyl $C_{1-4}$ alkyloxy), $R^2$ represents formyl, carboxyl, —COO—$C_{1-6}$ alkyl (preferably —COO—$C_{1-4}$ alkyl), or —CH$_2$OR$^5$, wherein $R^5$ represents a hydrogen atom, $C_{1-6}$ alkyl (preferably $C_{1-4}$ alkyl) or $C_{1-6}$ alkylcarbonyl (preferably $C_{1-4}$ alkylcarbonyl), $R^3$ represents a hydrogen atom and $R^4$ represents aralkyloxy (preferably phenyl $C_{1-4}$ alkyloxy), and
- a compound wherein $R^1$ represents a hydroxyl group or $C_{1-6}$ alkoxy (preferably $C_{1-4}$ alkoxy), $R^2$ represents aralkyloxy (preferably phenyl $C_{1-4}$ alkyloxy), $R^3$ represents a hydrogen atom and $R^4$ represents aralkyloxy (preferably phenyl $C_{1-4}$ alkyloxy).

Preparation of compounds

Some of the compounds represented by the formula (I) are known in the art, and may be prepared by processes previously described.

Preferred production processes will be described. The compounds represented by the formula (II) are embraced in the compounds represented by the formula (I) and, hence, can be prepared by the following production processes.

In the following processes, preferably, any functional group which does not participate in contemplated reactions is preferably protected. In this case, it would be apparent to a person having ordinary skill in the art that protective groups for this purpose may be those known in the art.

Process (A)

Among the triterpene derivatives represented by the formula (I), a compound represented by the following formula (Ia), wherein $R^{3a}$ represents a $C_{1-6}$ alkyl group, can be prepared in accordance with the following scheme:

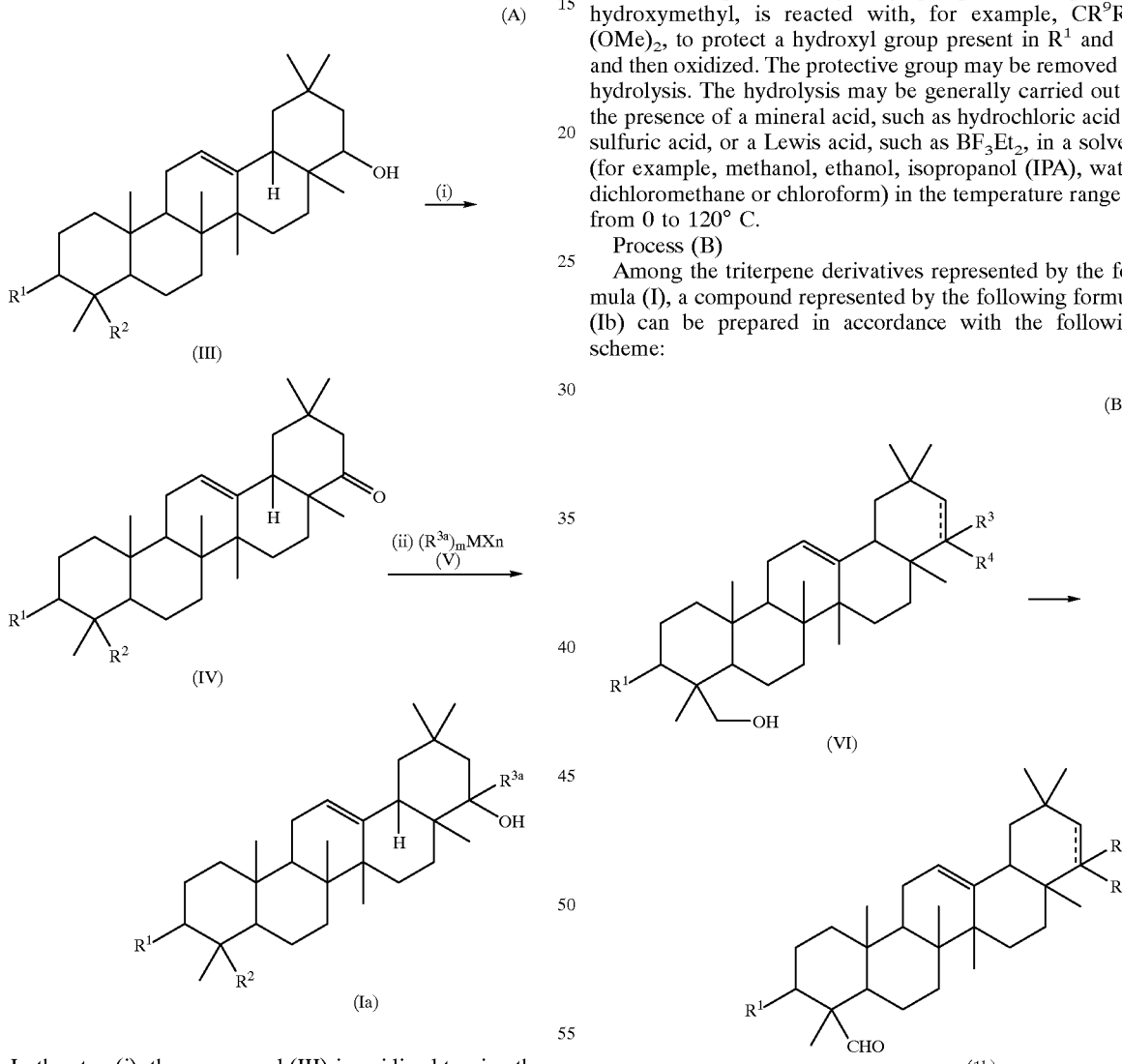

In the step (i), the compound (III) is oxidized to give the compound (IV). Oxidizing agents usable herein include, for example, pyridinium chromate, pyridinium dichromate, manganese dioxide, and dimethylsulfoxide (DMSO) oxidizing regents, such as DMSO-oxalyl chloride. Preferably, the oxidizing agent is used in an amount of 1 to 5 equivalents based on the compound (III). The reaction may be carried out in an inert solvent (for example, dichloromethane, chloroform, diethyl ether, or tetrahydrofuran (THF)) in the temperature range of −78 to 40° C.

In the step (ii), the compound of the formula (IV) is reacted with the compound of the formula (V), wherein $R^{3a}$ represents a $C_{1-6}$ alkyl group, M represents a metal, X represents a halogen or lithium, m is an integer of 1 to 4 and n is an integer of 0 to 3, to give the compound of the formula (1a). The reaction may be carried out in an inert solvent (for example, diethyl ether, THF, benzene, toluene, hexane, dimethylformamide (DMF), hexamethylphosphoric triamide, or dichloromethane) in the temperature range of from −78 to 20° C. Preferably, the compound of the formula (V) is used in an amount of 1 to 3 equivalents based on the compound of the formula (IV). Preferred examples of metals represented by M include lithium, magnesium, tin, zinc, boron, silicon, aluminum, and copper.

In the reactions according to the above scheme, preferably, the compound represented by the formula (III), wherein $R^1$ represents a hydroxyl group and $R^2$ represents hydroxymethyl, is reacted with, for example, $CR^9R^{10}$ $(OMe)_2$, to protect a hydroxyl group present in $R^1$ and $R^2$ and then oxidized. The protective group may be removed by hydrolysis. The hydrolysis may be generally carried out in the presence of a mineral acid, such as hydrochloric acid or sulfuric acid, or a Lewis acid, such as $BF_3Et_2$, in a solvent (for example, methanol, ethanol, isopropanol (IPA), water, dichloromethane or chloroform) in the temperature range of from 0 to 120° C.

Process (B)

Among the triterpene derivatives represented by the formula (I), a compound represented by the following formula (Ib) can be prepared in accordance with the following scheme:

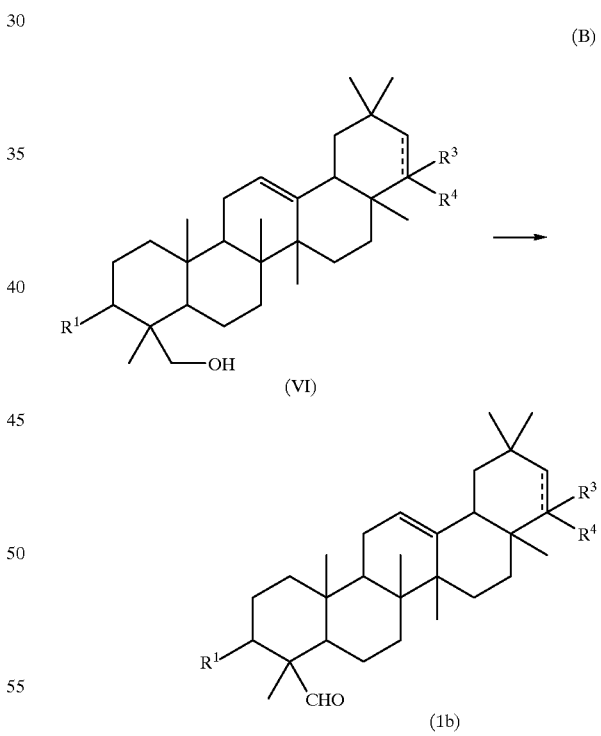

The compound of the formula (VI) may be oxidized with a suitable oxidizing agent to give the compound of the formula (1b). Oxidizing agents usable herein include, for example, pyridinium chromate, pyridinium dichromate, manganese dioxide, and dimethylsulfoxide (DMSO) oxidizing regents, such as DMSO-oxalyl chloride. Preferably, the oxidizing agent is used in an amount of 1 to 5 equivalents based on the compound (VI). The reaction may be carried out in an inert solvent (for example, dichloromethane, chloroform, diethyl ether, or tetrahydrofuran (THF)) in the temperature range of −78 to 40° C.

Process (C)

Among the triterpene derivatives represented by the formula (I), a compound represented by the following formula (Ic) can be prepared by oxidizing the compound of the formula (1b):

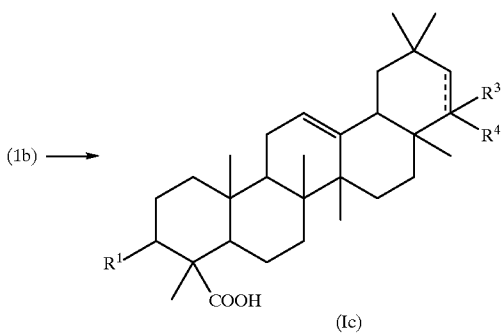

(C)

The reaction may be carried out in an inert solvent (for example, DMF, tert-butanol, acetone, or water) in the presence of an oxidizing agent (for example, pyridinium dichromate, Jones reagent, potassium permanganate, or sodium chlorite) in the temperature range of from 0 to 60° C. In general, the oxidizing agent is preferably used in an amount of 1 to 30 equivalents based on the compound of the formula (Ib).

Process (D)

Among the triterpene derivatives represented by the formula (I), a compound represented by the following formula (Id) can be prepared by the following process.

(D)

In the step (i), the compound of the formula (IV) is reacted with a methylenating agent (for example, $Ph_3P=CH_2$, Tabbe reagent, or Nysted reagent) to give the compound of the formula (VII). Preferably, the methylenating agent is used in an amount of 1 to 10 equivalents based on the compound of the formula (IV). The reaction may be carried out in an inert solvent (for example, dichloromethane, chloroform, diethyl ether, THF, DMF, or DMSO) in the temperature range of from −78 to 40° C. If necessary, a Lewis acid, such as titanium tetrachloride, may be added to the reaction system to accelerate the reaction.

Then, in the step (ii), the compound (VII) may be catalytically reduced in the presence of a catalyst to give the compound of the formula (Id). The reaction may be carried out in an inert solvent (for example, methanol, ethanol, THF, dioxane, dichloromethane, chloroform, or water), usually in a hydrogen atmosphere of 1 to 4 atm, at room temperature. For example, palladium-carbon, palladium black, or palladium hydroxide-carbon may be used as the catalyst in an amount of 0.1 to 0.6 equivalent.

Process (E)

Among the triterpene derivatives represented by the formula (I), a compound represented by the formula (Ie), wherein $R^4$ represents formyl, can be prepared by the following process.

(E)

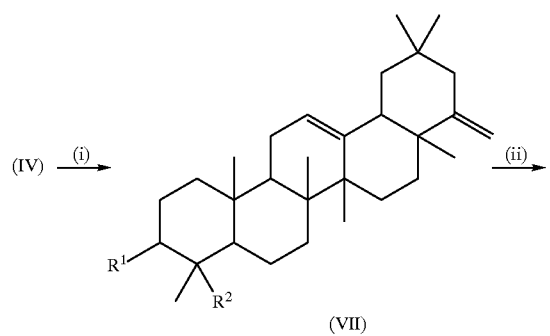

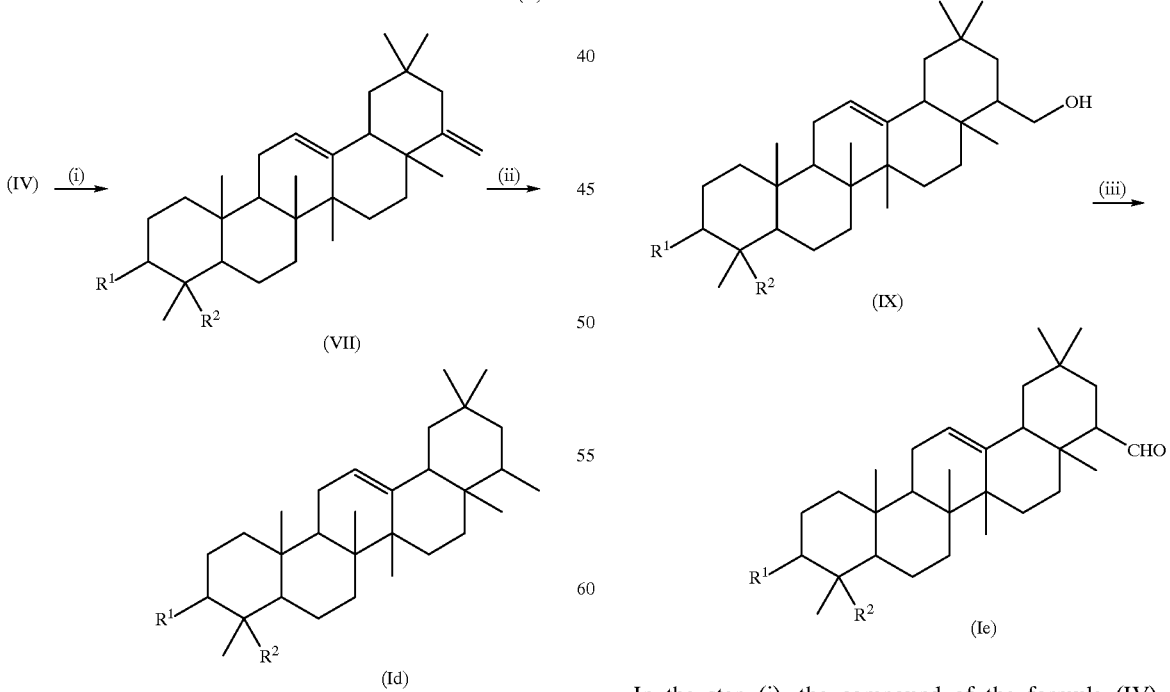

In the step (i), the compound of the formula (IV) is methylenated according to the process (D).

Then, in the step (ii), the compound of the formula (IV) is reacted with a hydroboration reagent, and the reaction product is then oxidized to give the compound of the formula (IX). Hydroboration reagents usable herein include, for example, BH$_3$-THF, thexylborane, 9-borabicyclo(3,3,1) nonane. Preferably, this reagent is used in an amount of 1 to 10 equivalents based on the compound of the formula (IV). The reaction may be carried out in an inert solvent (for example, diethyl ether or THF) in the temperature range of from 0° C. to room temperature.

In the oxidation reaction, an oxidizing agent (for example, sodium hydroxide or 30% hydrogen peroxide) is added to the reaction mixture, and the reaction is carried out at 0° C.

The compound of the formula (IX) thus obtained is converted, by oxidation in the step (iii), to the compound of the formula (Ie). Oxidizing agents usable herein include, for example, pyridinium chromate, pyridinium dichromate, manganese dioxide, and dimethylsulfoxide (DMSO) oxidizing regents, such as DMSO-oxalyl chloride. Preferably, the oxidizing agent is used in an amount of 1 to 5 equivalents based on the compound (IX). The reaction may be carried out in an inert solvent (for example, dichloromethane, chloroform, diethyl ether, or THF) in the temperature range of −78 to 40° C.

Process (F)

Among the triterpene derivatives represented by the formula (I), a compound represented by the following formula (If) can be prepared by oxidizing the compound of the formula (Ie):

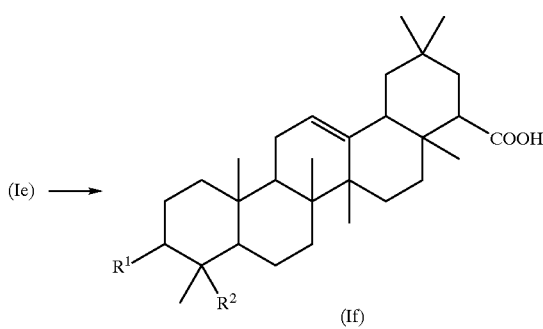

Oxidizing agents usable herein include pyridinium dichromate, Jones reagent, potassium permanganate, and sodium chlorite. The oxidizing agent is used in an amount of 1 to 30 equivalents based on the compound of the formula (Ie). The oxidation reaction is carried out in an inert solvent (for example, DMF, tert-butanol, acetone, or water) in the temperature range of from 0 to 60° C.

Process (G)

Among the triterpene derivatives represented by the formula (I), a compound represented by the following formula (Ig), wherein ═ ─ ─ represents a double bond, can be prepared by the following process:

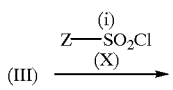

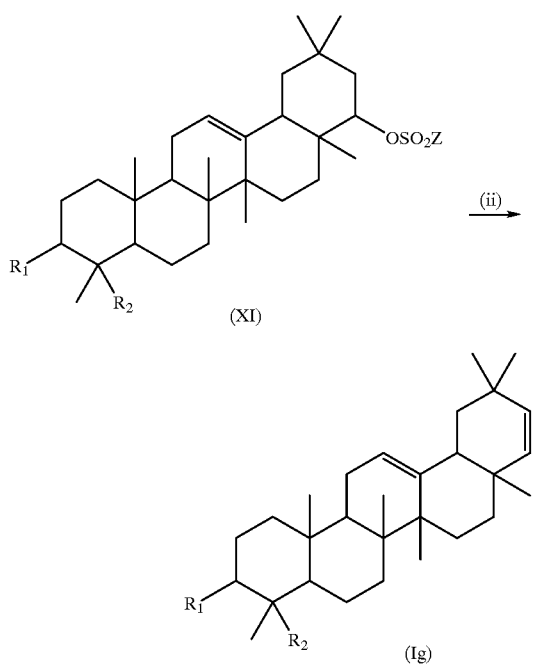

In the step (i), the compound of the formula (III) may be reacted with the compound of the formula (X): Z—SO$_2$Cl, wherein Z represents a C$_{1-6}$ alkyl group or an aryl group, to give the compound of the formula (XI). Preferred examples of the compound of the formula (X) include methanesulfonyl chloride, benzenesulfonyl chloride, and p-toluenesulfonyl chloride. The reaction is carried out in the presence of a suitable base in an inert solvent (for example, benzene, toluene, dichloromethane, chloroform, diethyl ether, THF, or DMF) in the temperature range of 0 to 60° C. Preferred bases include, for example, triethylamine, pyridine, 4-dimethylaminopyridine, and, preferably, the compound of the formula (X) and the base are used in an amount of 1 to 3 equivalents based on the compound of the formula (III).

In the step (ii), the compound of the formula (XI) thus obtained may be reduced with a suitable reducing agent to give the compound of the formula (Ig). Reducing agents usable herein include, for example, triethylboronlithium hydride. Preferably, the reducing agent is used in an amount of 1 to 5 equivalents based on the compound of the formula (XI). The reaction is carried out in an inert solvent (for example, diethyl ether, THF, benzene, toluene, or dichloromethane) in the temperature range of from −78 to 80° C.

Process (H)

Among the triterpene derivatives represented by the formula (I), a compound represented by the following formula (Ih) can be prepared by reducing the compound of the formula (Ig):

(Ig) → 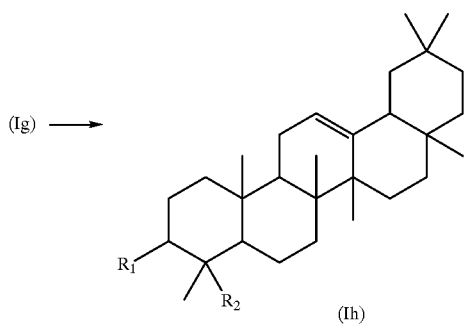
(Ih)

The reduction reaction may be carried out by catalytically reducing the compound (Ig) in the presence of a catalyst. The reaction may be carried out in an inert solvent (for example, methanol, ethanol, THF, dioxane, dichloromethane, chloroform, or water), usually in a hydrogen atmosphere of 1 to 4 atm, at room temperature. For example, palladium-carbon, palladium black, or palladium hydroxide-carbon may be used as the catalyst in an amount of 0.1 to 0.6 equivalent.

Process (I)

Among the triterpene derivatives represented by the formula (I), a compound represented by the formula (Ii), wherein $R^{12}$ is as defined above, can be prepared by the following process:

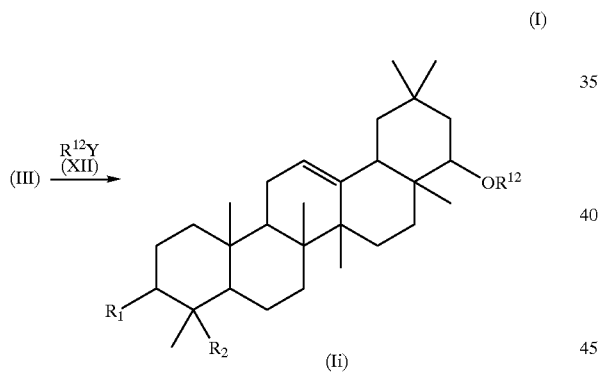

The compound of the formula (III) is reacted with the compound of the formula (XII): $R^{12}Y$, wherein $R^{12}$ is as defined above and Y represents a halogen atom, in the presence of a base to give the compound of the formula (Ii). The reaction is carried out in an inert solvent (for example, chloroform, dichloromethane, diethyl ether, THF, benzene, toluene, DMF, or DMSO) in the temperature range of from −78 to 60° C. Bases usable herein include, for example, pyridine, triethylamine, 4-dimethylaminopyridine, sodium hydride, potassium hydride, n-butyllithium, $NaCH_2SOCH_3$, and tert-BuOk. Preferably, the base and the compound of the formula (XII) are used in an amount of 1 to 10 equivalents based on the compound of the formula (III).

Process (J)

Among the triterpene derivatives represented by the formula (I), a compound represented by the following formula (Ij1), wherein $R^5$ is as defined above, and a compound of the formula (Ij2), wherein $R^{1a}$ represents $C_{1-6}$ alkyl, $C_{1-6}$ alkylcarbonyl, or aralkyl), can be prepared by the following process:

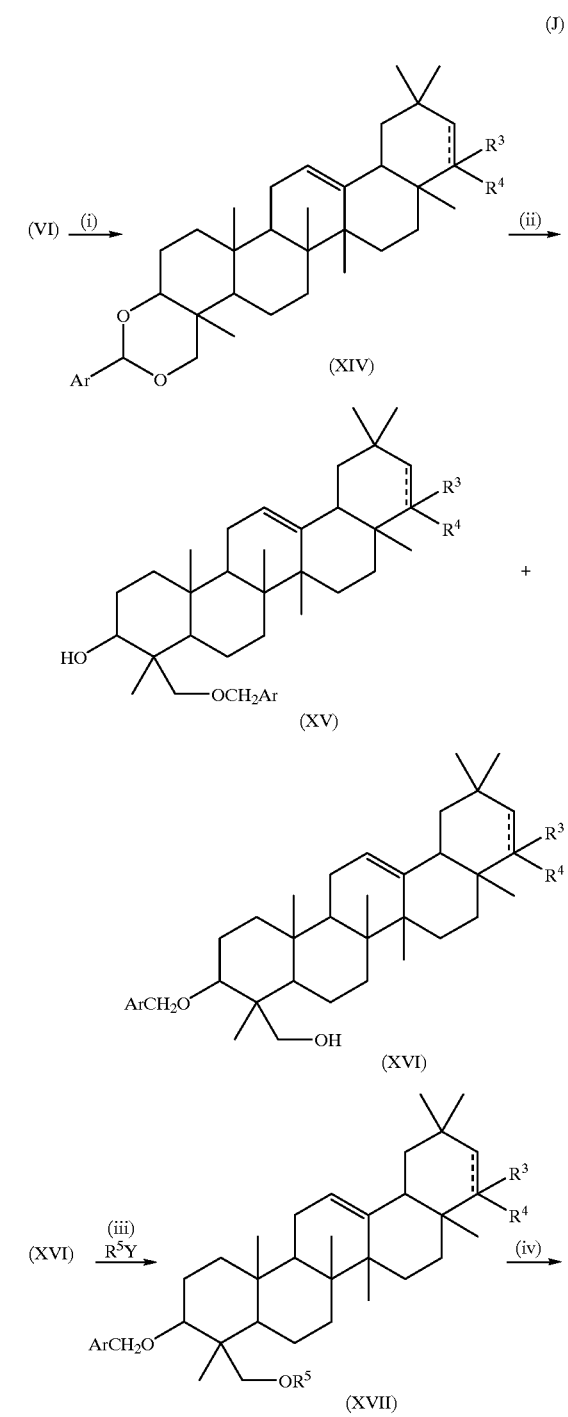

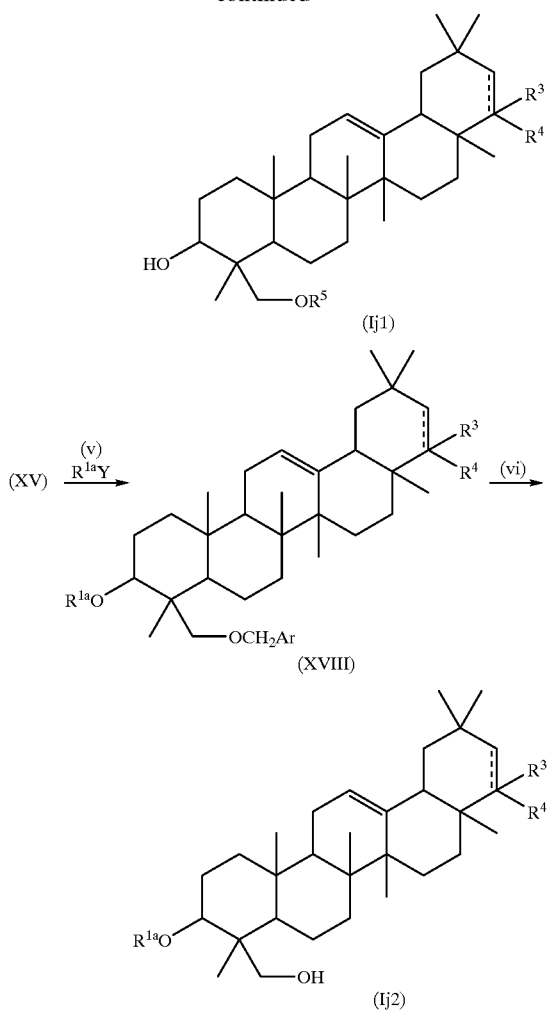

In the step (i), the compound of the formula (VI) is reacted with ArCH(OMe)$_2$ or ArCHO in the presence of an acid to give the compound of the formula (XIV). The reaction may be carried out in an inert solvent (for example, benzene, toluene, xylene, dichloromethane, chloroform, diethyl ether, THF, DMF, or acetone) in the temperature range of 0 to 120° C. Acid usable herein include hydrochloric acid, sulfuric acid, p-toluenesulfonic acid, and camphorsulfonic acid. Preferably, ArCH(OMe)$_2$ or ArCHO is used in an amount of 1 to 30 equivalents based on the compound of the formula (VI).

In the step (ii), the compound of the formula (XIV) thus obtained may be reduced with a suitable reducing agent to give the compound of the formula (XV) and the compound of the formula (XVI). Reducing agents usable herein include aluminum hydride, diisobutyl aluminum hydride, lithiumaluminum hydride-aluminum chloride. Preferably, the reducing agent is used in an amount of 1 to 10 equivalents based on the compound of the formula (XIX). The reaction is carried out in an inert solvent (for example, dichloromethane, chloroform, benzene, toluene, or diethyl ether) in the temperature range of from −30 to 40° C.

Subsequently, in the step (iii), the compound of the formula (XVI) thus obtained is reacted with a compound represented by the formula: R$^5$Y, wherein R$^5$ is as defined above and Y represents a halogen atom, in the presence of a base to give a compound of the formula (XVII). Bases usable herein include, for example, sodium hydride, potassium hydride, n-butyllithium, NaCH$_2$SOCH$_3$, tert-BuOk, triethylamine, pyridine, and 4-dimethylaminopyridine. Preferably, the base and the compound of the formula: R$^5$Y are used in an amount of 1 to 10 equivalents based on the compound of the formula (XVI). The reaction is carried out in an inert solvent (for example, diethyl ether, THF, benzene, toluene, DMF, DMSO, or dichloromethane) at −78 to 60° C.

In the step (iv), the compound of the formula (XVII) thus obtained may be catalytically reduced in the presence of a catalyst to give the compound of the formula (Ij1). The reaction may be carried out in an inert solvent (for example, methanol, ethanol, THF, dioxane, dichloromethane, chloroform, or water), usually in a hydrogen atmosphere of 1 to 4 atm, at room temperature. For example, palladium-carbon, palladium black, or palladium hydroxide-carbon may be used as the catalyst in an amount of 0.1 to 0.6 equivalent.

In the step (v), the compound of the formula (XV) may be reacted with a compound of the formula: R$^{1a}$Y, wherein R$^{1a}$ is as defined above and Y is a halogen atom, in the presence of a based to give the compound of the formula (XVIII). Bases usable herein include, for example, sodium hydride, potassium hydride, n-butyllithium, NaCH$_2$SOCH$_3$, tert-BuOk, triethylamine, pyridine, and 4-dimethylaminopyridine. Preferably, the base and the compound of the formula: R$^5$Y are used in an amount of 1 to 10 equivalents based on the compound of the formula (XVI). The reaction is carried out in an inert solvent (for example, diethyl ether, THF, benzene, toluene, DMF, DMSO, or dichloromethane) at −78 to 60° C.

In the step (vi), the compound of the formula (XVIII) thus obtained may be catalytically reduced in the presence of a catalyst to give the compound of the formula (Ij1). The reaction may be carried out in an inert solvent (for example, methanol, ethanol, THF, dioxane, dichloromethane, chloroform, or water), usually in a hydrogen atmosphere of 1 to 4 atm, at room temperature. For example, palladium-carbon, palladium black, or palladium hydroxide-carbon may be used as the catalyst in an amount of 0.1 to 0.6 equivalent.

Process (K)

Among the triterpene derivatives represented by the formula (I), a compound of the formula (Ik), wherein R$^7$ and R$^8$ are as defined above, can be prepared from the compound of the formula (Ib) by the following process:

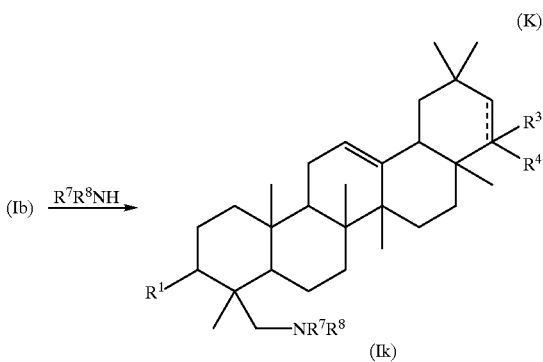

The compound of the formula (Ib) and a compound of the formula R$^7$R$^8$NH, wherein R$^7$ and R$^8$ are as defined above, are subjected to catalytic reduction in the presence of a catalyst. The reaction may be carried out in an inert solvent (for example, methanol, ethanol, THF, dioxane, dichloromethane, chloroform, or water), usually in a hydrogen atmosphere of 1 to 4 atm, at room temperature. For example, palladium-carbon, palladium black, or palladium hydroxide-carbon may be used as the catalyst in an amount of 0.1 to 0.6 equivalent.

Process (L)

Among the triterpene derivatives represented by the formula (I), a compound of the formula (II), wherein $R^6$ is as defined above, can be prepared from the compound of the formula (Ic) by esterification according to the following process:

(Ic) →

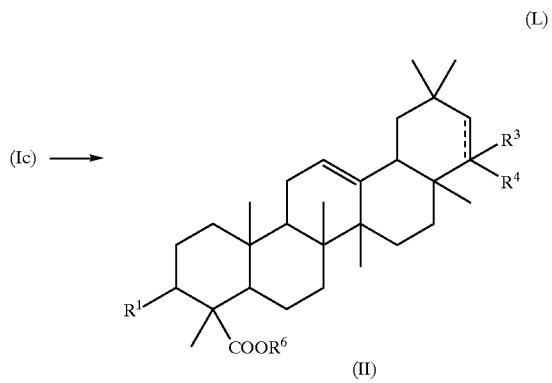

(II)

The esterification can be carried out by reacting the compound of the formula (Ic) with $R^6X$, wherein $R^6$ represents a $C_{1-6}$ alkyl group and X represents a halogen, in the presence of a base, or with $R^6OH$, wherein $R^6$ is as defined above, and a condensing agent in the presence of a base, or with diazomethane, trimethylsilyldiazomethane or the like to give the compound of the formula (II). Bases usable herein include sodium hydrogencarbonate, sodium carbonate, sodium hydride, cesium carbonate, triethylamine, pyridine, 4-dimethylaminopyridine, and DBU. Condensing agents usable herein include cyclohexylcarbodiimide. Preferably, the base, $R^6X$, $R^6OH$, and condensing agent are used in an amount of 1 to 2 equivalents based on the compound of the formula (Ic). The reaction may be carried out in an inert solvent (for example, diethyl ether, THF, benzene, toluene, DMF, dichloromethane, or MeOH) in the temperature range of 0 to 40° C.

EXAMPLES

The present invention will be described in more detail with reference to the following examples, though it is not limited to these examples only.

Compounds 1 to 73 listed in Table 1 described below were synthesized. Compounds 1, 4, 24, 25, 27, and 28 were produced according to a process described in Chem. Pharm. Bull., 36, 153 (1988), and compound 9 was produced according to a process described in Chem. Pharm. Bull., 24, 121 (1976), Chem. Pharm. Bull., 31, 664 (1983), and Chem. Pharm. Bull., 31, 674 (1983).

Example 1

22-Oxolean-12-ene-3β,24(4β)-diol (Compound 2)

Oxalyl chloride (0.4 ml) was dissolved in 10 ml of dichloromethane, and the solution was cooled to −78° C. A solution of 0.65 ml of DMSO in 2 ml of dichloromethane was added to the cooled solution, and the mixture was then stirred for 10 min. A solution of 1.5 g of compound 1 in 5 ml of dichloromethane was dropwise added to the reaction mixture, and the mixture was then stirred at −78° C. for 15 min. To the reaction mixture was added 2.1 ml of triethylamine, and the mixture was stirred at −78° C. for 5 min. The temperature of the reaction mixture was gradually raised to 0° C., diluted with water, and extracted with dichloromethane. The organic layer was washed with saturated sodium hydrogencarbonate and dried over magnesium sulfate. After the inorganic salt was removed by filtration, the filtrate was concentrated under reduced pressure. The resultant solid was purified by column chromatography on silica gel (n-hexane:ethyl acetate=10:1). The colorless solid (1.3 g) thus obtained was dissolved in 30 ml of methanol, 1 N hydrochloric acid was added thereto, and the mixture was stirred at room temperature for 30 min. The reaction mixture was diluted with dichloromethane, washed with water, and dried over magnesium sulfate. After the inorganic salt was removed by filtration, the filtrate was concentrated under reduced pressure to give 1.2 g (yield 86%) of compound 2 as a colorless solid.

NMR (CDCl$_3$) δ ppm 0.86 (3H, s), 0.90 (3H, s), 0.94 (3H, s), 0.99 (3H, s), 1.00 (3H, s), 1.22 (3H, s), 1.26 (3H, s), 0.88–2.58 (23H, m), 3.35, 4.21 (1H each, both d, J=11.1 Hz), 3.45 (1H, dd, J=4.4 Hz), 5.30 (1H, t-like).

MS EI (m/z): 456 (M$^+$)

Example 2

22α-Methylolean-12-ene-3β,22β,24(4β)-triol (Compound 3)

In 5 ml of anhydrous THF was dissolved 100 mg (0.22 mmol) of compound 2, and 670 μl of a diethyl ether solution of methyllithium (1.8 mol/l) was added thereto at −78° C. The mixture was stirred for one hr while gradually raising the temperature to 0° C. Water was added thereto, and the mixture was extracted with ethyl acetate. The organic layer was dried over magnesium sulfate. After the inorganic salt was removed by filtration, the filtrate was concentrated under reduced pressure. The residue was purified by column chromatography on silica gel (n-hexane:ethyl acetate 2:1) to give 62 mg (yield 60%) of compound 3.

NMR (CDCl$_3$) δ ppm 0.86 (3H, s), 0.89 (6H, s), 0.96 (3H, s), 1.07 (3H, s), 1.10 (3H, s), 1.16 (3H, s), 1.25 (3H, s), 0.84–2.86 (24H, m), 3.35 (1H, t, J=10.2 Hz), 3.44 (1H, m), 4.20 (1H, d, J=11.1 Hz), 5.23 (1H, t-like).

MS EI (m/z): 472 (M$^+$)

Example 3

3β,22β-Dibenzyloxy-24(4β)-triphenylmethyloxymethylolean-12-ene (Compound 5)

In 5 ml of anhydrous DMF was dissolved 95 mg of compound 4.83 mg of 60% sodium hydride was added to the solution, and the mixture was then stirred at room temperature for 1.5 hr. Thereafter, 75 μl of benzyl bromide was added to the reaction mixture, and the mixture was then stirred at 40° C. for 5 hr. The reaction mixture was diluted with ethyl acetate, washed thrice with water, and dried over magnesium sulfate. After the inorganic salt was removed by filtration, the filtrate was concentrated under reduced pressure. The oil thus obtained was purified by column chromatography on silica gel (n-hexane:ethyl acetate=10:1) to give 118 mg (yield 65%) of compound 5 as a colorless solid.

NMR (CDCl$_3$) δ ppm 0.33 (3H, s), 0.82 (3H, s), 0.88 (3H, s), 0.92 (3H, s), 1.03 (3H, s), 1.08 (3H, s), 1.34 (3H, s), 0.70–2.15 (21H, m), 2.93–2.97 (1H, m), 3.06–3.07 (1H, m), 3.17 (1H, d, J=9.2 Hz), 3.53 (1H, d, J=9.2 Hz), 4.32 (1H, d, J=11.9 Hz), 4.38 (1H, d, J=11.9 Hz), 4.61 (1H, d, J=11.9 Hz), 4.63 (1H, d, J=11.9 Hz), 5.17 (1H, t-like), 7.19–7.50 (25H, m).

MS FD (m/z): 881(M$^+$+1)

Example 4

3β,22β-Dibenzyloxyolean-12-en-24(4β)-ol
(Compound 6)

In a mixed solution of 10 ml of methanol and 2 ml of acetone was dissolved 440 mg of compound 5. Concentrated hydrochloric acid (0.4 ml) was further added thereto, and the mixture was refluxed for 30 min. After water was added to the reaction mixture, the mixture was neutralized with 1 N sodium hydroxide and extracted thrice with dichloromethane. The organic layer was dried over magnesium sulfate. After the inorganic salt was removed by filtration, the filtrate was concentrated under reduced pressure. The oil thus obtained was purified by column chromatography on silica gel (n-hexane:ethyl acetate=10:1) to give 231 mg (yield 72%) of compound 6 as an oil.

NMR (CDCl$_3$) δ ppm 0.88 (3H, s), 0.89 (3H, s), 0.93 (3H, s), 0.94 (3H, s), 1.05 (3H, s), 1.11 (3H, s), 1.21 (3H, s), 0.85–2.18 (22H, m), 3.07–3.08 (1H, m), 3.18–3.24 (2H, m), 4.16 (1H, d, J=10.5 Hz), 4.32 (1H, d, J=11.7 Hz), 4.39 (1H, d, J=11.7 Hz), 4.62 (1H, d, J=11.7 Hz), 4.67 (1H, d, J=11.7 Hz), 5.22 (1H, t-like), 7.26–7.34 (10H, m).

MS SIMS (m/z): 639 (M$^+$+1)

Example 5

3β,22β-Dibenzyloxy-24(4β)-oxolean-12-ene
(Compound 7)

Oxalyl chloride (0.15 ml) was dissolved in 4 ml of dichloromethane, and the solution was then cooled to −78° C. A solution of 0.23 ml of DMSO in dichloromethane was added to the cooled solution, and the mixture was then stirred for 10 min. A solution of 128 mg of compound 6 in 2 ml of dichloromethane was added to the reaction mixture, and the mixture was then stirred at −78° C. for 15 min. To the reaction mixture was added 0.7 ml of triethylamine, and the mixture was stirred at −78° C. for 5 min. The temperature of the reaction mixture was gradually raised to 0° C., diluted with water, and extracted with dichloromethane. The organic layer was washed with saturated sodium hydrogencarbonate and dried over anhydrous magnesium sulfate. After the inorganic salt was removed by filtration, the filtrate was concentrated under reduced pressure. The resultant oil was purified by column chromatography on silica gel (n-hexane:ethyl acetate=10:1) to give 104 mg (yield 82%) of compound 7 as a colorless foam substance.

NMR (CDCl$_3$) δ ppm 0.83 (3H, s), 0.89 (3H, s), 0.93 (3H, s), 0.94 (3H, s), 1.04 (3H, s), 1.10 (3H, s), 1.21 (3H, s), 0.85–2.18 (21H, m), 3.07 (1H, dd, J=3.1 Hz, 3.1 Hz), 3.18 (1H, dd, J=5.1 Hz, 5.1 Hz), 4.20, 4.61 (1H, each, both d, J=11.7 Hz), 5.23 (1H, t-like), 7.22–7.35 (10H, m), 10.07 (1H, s).

MS SIMS (m/z): 637 (M$^+$+1)

Example 6

24(4β)-Oxolean-12-ene-3β,22β-diol (Compound 8)

In 1 ml of methanol was dissolved 30 mg of compound 7, and 30 mg of 20% Pd(OH)$_2$—C was added to the solution. The mixture was subjected to catalytic reduction at room temperature under atmospheric pressure for one hr. After the reaction mixture was filtered through Celite, the filtrate was concentrated under reduced pressure to give 21 mg (yield 100%) of compound 8.

NMR (CDCl$_3$) β ppm 0.88 (6H, s), 0.92 (3H, s), 1.00 (3H, s), 1.04 (3H, s), 1.13 (3H, s), 1.30 (3H, s), 0.97–2.12 (22H, m), 3.12–3.20 (1H, m), 3.44 (1H, t, J=5.1 Hz), 5.26 (1H, t-like), 9.76 (1H, d, J=2.4 Hz).

MS EI (m/z): 456 (M$^+$)

Example 7

3β,22β-Dibenzyloxyolean-12-en-24(4β)-oic acid
(Compound 10)

In 6 ml of tert-butanol was dissolved 20 mg of compound 7, and 1.5 ml of 2-methyl-2-butene was added thereto. A solution of 250 mg of sodium chlorite and 250 mg of monosodium phosphate in 2.5 ml of water was added to the reaction solution, and the mixture was then stirred at room temperature overnight. After the reaction mixture was concentrated under reduced pressure, the concentrate was extracted with ethyl acetate. The organic layer was dried over magnesium sulfate. After the inorganic salt was removed by filtration, the filtrate was concentrated under reduced pressure. The oil thus obtained was purified by column chromatography on silica gel (n-hexane:ethyl acetate=5:1) to give 6.8 mg (yield 34%) of compound 10 as colorless solid.

NMR (CDCl$_3$) β ppm 0.89 (3H, s), 0.94 (3H, s), 0.95 (3H, s), 1.02 (3H, s), 1.04 (3H, s), 1.10 (3H, s), 1.40 (3H, s), 0.85–2.19 (21H, m), 3.05–3.09 (1H, m), 3.15–3.19 (1H, m), 4.32 (1H, d, J=11.83 Hz), 4.56 (1H, d, J=11.83 Hz), 4.61 (1H, d, J=11.83 Hz), 4.85 (1H, d, J=11.83 Hz), 5.23 (1H, t-like), 7.23–7.52 (10H, m).

MS EI (m/z): 652 (M$^+$)

Example 8

3β,22β-Dihydroxyolean-12-en-24(4β)-oic acid
(Compound 11)

Compound 10 (5 mg) was dissolved in a mixed solvent of 0.5 ml of methanol and 0.5 ml of dichloromethane, and 5 mg of 20% Pd(OH)$_2$—C was added to the solution. The mixture was subjected to catalytic reduction at room temperature under atmospheric pressure for 45 min. After the reaction mixture was filtered through Celite, the filtrate was concentrated under reduced pressure to give 3.3 mg (yield 92%) of compound 11 as a foam substance.

NMR (CDCl$_3$) δ ppm 0.85 (3H, s), 0.92 (3H, s), 0.93 (3H, s), 1.00 (3H, s), 1.02 (3H, s), 1.11 (3H, s), 1.41 (3H, s), 0.87–2.08 (21H, m), 3.09–3.12 (1H, m), 3.40–3.43 (1H, m), 5.27 (1H, t-like).

MS SIMS (m/z): 473 (M$^+$+1)

Example 9

22-Methyleneolean-12-ene-3β,24(4β)-diol
(Compound 12)

In 12 ml of Nysted reagent was suspended 1.0 g of compound 2, and the suspension was cooled to −78° C. A solution (5 ml) of titanium tetrachloride (1.0 M) in dichloromethane solution was added by portions to the cooled suspension. The temperature of the reaction mixture was returned to room temperature, and the reaction mixture was then stirred overnight. While the reaction mixture was stirred under ice cooling, 6 N hydrochloric acid was added by portions thereto. The mixture was extracted thrice with chloroform, and the organic layer was then dried over anhydrous magnesium sulfate. After the inorganic salt was removed by filtration, the filtrate was concentrated under reduced pressure. The resultant solid was purified by column chromatography on silica gel (n-hexane:ethyl acetate=2:1) to give 518 mg (yield 52%) of compound 12 as a colorless solid.

NMR (CDCl$_3$) δ ppm 0.78 (3H, s), 0.89 (3H, s), 0.90 (3H, s), 0.95 (3H, s), 1.03 (3H, s), 1.17 (3H, s), 1.25 (3H, s), 0.84–2.20 (21H, m), 2.39 (1H, brs), 2.72 (1H, brs), 3.32–3.37 (1H, m), 3.43–3.46(1H, m), 4.21 (1H, d, J=11.10 Hz), 5.27 (1H, t-like).

MS EI (m/z): 454 (M$^+$)

Example 10

22-Methylolean-12-ene-3β,24(4β)-diol (Compound 13)

Compound 12 (29 mg) was dissolved in a mixed solvent of 1 ml of methanol and 9 ml of dichloromethane, and 20 mg of 20% Pd(OH)$_2$—C was added to the solution. The mixture was subjected to catalytic reduction at room temperature under atmospheric pressure for one hr. After the reaction mixture was filtered through Celite, the filtrate was concentrated under reduced pressure to give 27 mg (yield 93%) of compound 13 as a colorless solid.

NMR (CDCl$_3$) δ ppm 0.80 (3H, s), 0.86 (6H, s), 0.89 (3H, s), 0.90 (3H, s), 0.93 (3H, s). 1.13 (3H, s), 1.25 (3H, s), 0.64–1.94 (22H, m), 3.35 (1H, d, J=10.52 Hz), 3.42–3.46 (1H, m), 4.20 (1H, d, J=10.52 Hz), 5.17 (1H, t-like).

MS EI (m/z): 456 (M$^+$)

Example 11

22-Hydroxymethylolean-12-ene-3β,24(4β)-diol (Compound 14)

In 7 ml of anhydrous THF was dissolved 300 mg of compound 12, and 3.3 ml of a solution of BH$_3$-THF (1.0 M) in THF was added to the solution. The mixture was then stirred at room temperature overnight. While the reaction mixture was stirred under ice cooling, 3 ml of 10% hydroxide solution was added thereto, and 3 ml of 30% hydrogen peroxide was added thereto over a period of 5 min. The mixture was stirred under ice cooling for 1.5 hr, water was added thereto. The mixture was extracted with ethyl acetate. The organic layer was washed with saturated saline and then dried over magnesium sulfate. After the inorganic salt was removed by filtration, the filtrate was concentrated under reduced pressure. The residue was purified by column chromatography on silica gel (n-hexane:ethyl acetate=1:1) to give 245 mg (yield 79%) of compound 14.

NMR (CDCl$_3$) δ ppm 0.70 (3H, s), 0.90 (3H, s), 0.91 (3H, s), 0.92 (3H, s), 0.96 (3H, s), 1.05 (3H, s), 1.25 (3H, s), 0.84–1.87 (22H, m), 3.28–3.35 (2H, m), 3.42–3.47 (1H, m), 3.65–3.70 (1H, m), 4.20 (1H, d, J=11.10 Hz), 5.25 (1H, t-like).

MS EI (m/z): 472 (M$^+$)

Example 12

22-Hydroxymethyl-3,24(4β)-isopropylidenedioxyolean-12-ene (Compound 15)

In 13 ml of acetone was dissolved 200 mg of compound 14, and 10 ml of 2,2-dimethoxypropane and 3 mg of camphorsulfonic acid were added to the solution. The mixture was then stirred at 37° C. overnight. After the reaction mixture was concentrated under reduced pressure, the residue was dissolved in ethyl acetate, a small amount of silica gel was added thereto. The mixture was then stirred at room temperature for two days. The reaction solution was concentrated under reduced pressure. The residue was purified by column chromatography on silica gel (n-hexane:ethyl acetate=5:1) to give 105 mg (yield 48%) of compound 15 as a colorless solid.

NMR (CDCl$_3$) δ ppm 0.70 (3H, s), 0.91 (3H, s), 0.95 (3H, s), 0.96 (3H, s), 1.06 (3H, s), 1.17 (3H, s), 1.21 (3H, s), 1.37 (3H, s), 1.43 (3H, s), 0.87–2.04 (22H, m), 3.21 (1H, d, J=11.54 Hz), 3.32 (1H, t, J=10.5 Hz), 3.45 (1H, dd, J=4.62 Hz, 9.24 Hz), 3.67 (1H, dd, J=10.52 Hz, 10.52 Hz), 4.03 (1H, d, J=11.54 Hz), 5.27 (1H, t-like).

MS EI (m/z): 512 (M$^+$)

Example 13

22-Formyl-3β,24(4β)-isopropylidenedioxyolean-12-ene (Compound 16)

The procedure of Example 5 was repeated, except that 105 mg of compound 15 was used as the starting compound. Thus, 91 mg (yield 87%) of compound 16 was prepared.

NMR (CDCl$_3$) δ ppm 0.87 (3H, s), 0.90 (3H, s), 0.96 (3H, s), 0.99 (3H, s), 1.10 (3H, s), 1.18 (3H, s), 1.21 (3H, s), 1.37 (3H, s), 1.43 (3H, s), 0.88–2.10 (22H, m), 3.22 (1H, d, J=11.72 Hz), 3.45–3.48 (1H, m), 4.03 (1H, d, J=11.72 Hz), 5.30 (1H, s), 9.80 (1H, s).

MS EI (m/z) δ ppm 510 (M$^+$)

Example 14

22-Formylolean-12-ene-3β,24(4β)-diol (Compound 17)

Compound 16 (10 mg) was dissolved in a mixed solvent of 1.0 ml of methanol and 1.0 ml of dichloromethane, 50 μl of 1 N hydrochloric acid was added to the solution under ice cooling. The mixture was then stirred for 10 min. The reaction mixture was diluted with ethyl acetate, washed with water and a saturated aqueous sodium hydrogencarbonate, and then dried over anhydrous magnesium sulfate. After the inorganic salt was removed by filtration, the filtrate was concentrated under reduced pressure. The residue was dissolved in a mixed solvent of 2 ml of acetone and 0.2 ml of water, a small amount of camphorsulfonic acid was added thereto. The mixture was then stirred at room temperature overnight. After the reaction solution was concentrated under reduced pressure, the residue was dissolved in dichloromethane. The solution was washed with water and saturated aqueous sodium hydrogencarbonate and then dried over magnesium sulfate. After the inorganic salt was removed by filtration, the filtrate was concentrated under reduced pressure to give 7 mg (yield 78%) of compound 17 as a colorless solid.

NMR (CDCl$_3$) δ ppm 0.79 (3H, s), 0.83 (6H, s), 0.84 (3H, s), 0.92 (3H, s), 1.02 (3H, s), 1.18 (3H, s), 0.77–2.03 (22H, m), 2.41 (1H, brs), 2.67 (1H, brs), 3.30 (1H, brs), 3.37 (1H, d, J=11.43 Hz), 4.13 (1H, d, J=11.43 Hz) 5.21 (1H, t-like), 9.72 (1H, s).

MS FD (m/z): 471 (M$^+$+1)

Example 15

22—Carboxy-3β,24(4β)-isopropylidenedioxyolean-12-ene (Compound 18)

The procedure of Example 7 was repeated, except that 20 mg of compound 16 was used as the starting compound. Thus, 21 mg (yield 99%) of compound 18 was prepared.

NMR (CDCl$_3$) δ ppm 0.83 (3H, s), 0.90 (3H, s), 0.95 (3H, s), 0.99 (3H, s), 1.07 (3H, s), 1.17 (3H, s), 1.21 (3H, s), 1.38 (3H, s), 1.44 (3H, s), 0.87–2.24 (22H, m), 3.22 (1H, d, J=11.73 Hz), 3.45–3.48 (1H, m), 4.03 (1H, d, J=11.73 Hz), 5.30 (1H, s).

MS EI (m/z): 526 (M$^+$)

Example 16

22-Carboxyolean-12-ene-3β,24(4β)-diol (Compound 19)

Compound 18 (20 mg) was dissolved in a mixed solvent of 2 ml of methanol and 1 ml of dichloromethane, 0.2 ml of 1 N hydrochloric acid was added to the solution under ice cooling. The mixture was then stirred for 10 min. The reaction mixture was diluted with ethyl acetate, washed with water, and dried over magnesium sulfate. After the inorganic salt was removed by filtration, the filtrate was concentrated under reduced pressure. The resultant solid was purified by column chromatography on silica gel (n-hexane:methanol= 10:1) to give 12 mg (yield 64%) of compound 19 as a colorless foam substance.

NMR (CDCl$_3$) δ ppm 0.81 (3H, s), 0.90 (9H, s), 0.98 (3H, s), 1.06 (3H, s), 1.23 (3H, s), 0.83–2.21 (22H, m), 3.32 (1H, d, J=11.1 Hz), 3.40 (1H, dd, J=4.16 Hz, 11.38 Hz), 4.20 (1H, d, J=11.1 Hz), 5.28 (1H, t-like).

MS FD (m/z): 486 (M$^+$)

Example 17

3β,24(4β)-Isopropylidenedioxy-22β-tosyloxyolean-12-ene (Compound 20)

Compound 1 (500 mg) was dissolved in pyridine, 287 mg of p-toluenesulfonyl chloride and a catalytic amount of 4-dimethylaminopyridine were added to the solution. The mixture was then stirred at room temperature overnight. After water was added to the reaction mixture, the mixture was extracted with ethyl acetate. The organic layer was dried over magnesium sulfate. After the inorganic slat was removed by filtration, the filtrate was concentrated under reduced pressure to give 654 mg (yield 100%) of compound 20 as a colorless solid.

NMR (CDCl$_3$) δ ppm 0.76 (3H, s), 0.84 (9H, s), 0.94 (3H, s), 0.96 (3H, s), 1.10 (3H, s), 1.14 (3H, s), 1.21 (3H, s), 1.37 (3H, s), 1.44 (3H, s), 0.78–2.10 (21H, m), 2.45 (3H, s), 3.22 (1H, d, J=11.65 Hz), 3.43–3.46 (1H, m), 4.03 (1H, d, J=11.65 Hz), 4.34–4.37 (1H, m), 5.22 (1H, t-like).

MS FD (m/z): 652 (M$^+$)

Example 18

3β,24(4β)-Isopropylidenedioxyolean-12,21-diene (Compound 21)

To 65 mg of compound 20 was added 2 ml of triethylboronlithium hydride (1.0 M THF solution) under ice cooling, and the mixture was then stirred at 65° C. for one hr. The temperature of the reaction mixture was returned to room temperature. After water was added thereto, the mixture was extracted with ethyl acetate. The organic layer was dried over magnesium sulfate. After the inorganic salt was removed by filtration, the filtrate was concentrated under reduced pressure. The resultant solid was purified by column chromatography on silica gel (n-hexane:ethyl acetate=10:1) to give 38 mg (yield 79%) of compound 21 as a colorless solid.

NMR (CDCl$_3$) δ ppm 0.88 (3H, s), 0.96 (9H, s), 0.98 (3H, s), 0.99 (3H, s), 1.12 (3H, s), 1.17 (3H, s), 1.22 (3H, s), 1.38 (3H, s), 1.44 (3H, s), 0.90–2.13 (19H, m), 3.23 (1H, d, J=11.54 Hz), 3.45–3.48 (1H, m), 4.05 (1H, d, J=11.54 Hz), 5.20–5.32 (3H, m).

MS EI (m/z): 480 (M$^+$)

Example 19

Olean-12,21-diene-3β,24(4β)-diol (Compound 22)

Compound 21 (48 mg) was dissolved in a mixed solvent of 1 ml of methanol and 1 ml of dichloromethane, 0.5 ml of 1 N hydrochloric acid was added to the solution. The mixture was then stirred for one hr. The reaction mixture was diluted with dichloromethane, washed with water, and dried over magnesium sulfate. After the inorganic salt was removed by filtration, the filtrate was concentrated under reduced pressure to give 36 mg (yield 82%) of compound 22 as a colorless solid.

NMR (CDCl$_3$) δ ppm 0.87 (3H, s), 0.90 (3H, s), 0.94 (3H, s), 0.95 (3H, s), 0.98 (3H, s), 1.11 (3H, s), 1.25 (3H, s), 0.84–2.13 (19H, m), 2.36 (1H, d, J=4.10 Hz), 2.68 (1H, d, J=6.67 Hz), 3.32–3.37 (1H, m), 3.43–3.48 (1H, m), 4.21 (1H, d, J=11.28 Hz), 5.20–5.30 (3H, m).

MS EI (m/z): 440 (M$^+$)

Example 20

Olean-12-ene-3β,24(4β)-diol (Compound 23)

Compound 21 (30 mg) was dissolved in a mixed solvent of 2 ml of methanol and 1 ml of dichloromethane, 5 mg of 20% Pd(OH)$_2$—C was added to the solution. The mixture was then subjected to catalytic reduction under atmospheric pressure overnight. After the reaction mixture was filtered, the filtrate was concentrated under reduced pressure to give 26 mg (yield 93%) of compound 23 as a colorless solid.

NMR (CDCl$_3$) δ ppm 0.82 (3H, s), 0.87 (6H, s), 0.89 (3H, s), 0.93 (3H, s), 1.13 (3H, s), 1.25 (3H, s), 1.25 (3H, s), 0.78–2.03 (23H, m), 2.37 (1H, d, J=4.16 Hz), 2.71 (1H, dd, J=2.50 Hz, 8.88 Hz), 3.32–3.37 (1H, m), 3.42–3.48 (1H, m), 4.21 (1H, d, J=10.88 Hz), 5.18 (1H, t-like).

MS EI (m/z): 442 (M$^+$)

Example 21

3β,24(4β)-Isopropylidenedioxy-22β-methoxyolean-12-ene (Compound 26)

Compound 1 (300 mg) was dissolved in 5 ml of THF, 130 mg of 55% sodium hydride was added thereto, and the mixture was then stirred at room temperature for one hr. Thereafter, the 2 ml of methyl iodide was further added to the reaction solution. The mixture was stirred overnight. The reaction mixture was diluted with ethyl acetate, washed with water, and dried over magnesium sulfate. After the inorganic salt was removed by filtration, the filtrate was concentrated under reduced pressure. The residue was purified by column chromatography on silica gel (n-hexane:ethyl acetate=10:1) to give 285 mg (yield 93%) of compound 26 as a colorless foam substance.

NMR (CDCl$_3$) δ ppm 0.86 (3H, s), 0.90 (3H, s), 0.99 (3H, s), 1.00 (3H, s), 1.11 (3H, s), 1.15 (3H, s), 1.22 (3H, s), 1.37 (3H, s), 1.44 (3H, s), 0.83–2.10 (21H, m), 2.80–2.83 (1H, m), 3.23 (1H, d, J=11.8 Hz), 3.28 (3H, s), 3.44–3.47 (1H, m), 4.06 (1H, d, J=11.8 Hz), 5.23 (1H, t-like).

MS FD (m/z): 512 (M$^+$).

Example 22

22β-Methoxyolean-12-ene-3β,24(4β)-diol (Compound 27)

Compound 26 (280 mg) was dissolved in THF, 0.66 ml of boron trifluoride ethyl ether was added to the solution, and the mixture was stirred at room temperature for one hr. The reaction mixture was neutralized with a saturated aqueous sodium hydrogencarbonate solution and extracted with ethyl acetate. The organic layer was dried over magnesium sulfate. After the inorganic salt was removed by filtration, the solution was concentrated under reduced pressure. The residue was purified by column chromatography on silica gel (n-hexane:ethyl acetate=2:1) to give 203 mg (yield 79%) of compound 27 as a colorless solid.

NMR (CDCl$_3$) δ ppm 0.85 (3H, s), 0.89 (3H, s), 0.90 (3H, s), 0.94 (3H, s), 1.00 (3H, s), 1.11 (3H, s), 1.25 (3H, s), 0.80–2.10 (21H, m), 2.80–2.82 (1H, m), 3.28 (3H, s), 3.33 (1H, d, J 11.1 Hz), 3.42–3.45 (1H, m), 5.22 (1H, t-like).

MS EI (m/z): 472 (M$^+$)

Example 23

22β-Benzyloxy-3β,24(4β)-isopropylideneoxyolean-12-ene (Compound 30)

Compound 1 (50 mg) was dissolved in 2 ml of anhydrous DMF, 20 mg of 60% sodium hydride was added to the solution, and the mixture was stirred at room temperature for one hr. Thereafter, 85 μ of benzyl bromide was added thereto, and the mixture was stirred overnight. The reaction mixture was diluted with ethyl acetate, washed with water, and dried over magnesium sulfate. After the inorganic salt was removed by filtration, the filtrate was concentrated under reduced pressure. The residue was purified by column chromatography on silica gel (n-hexane:ethyl acetate=10:1) to give 34 mg (yield 58%) of compound 30 as a colorless solid.

NMR (CDCl$_3$) δ ppm 0.89 (3H, s), 0.94 (3H, s), 0.99 (3H, s), 1.04 (3H, s), 1.12 (3H, s), 1.15 (3H, s), 1.22 (3H, s), 1.37 (3H, s), 1.44 (3H, s), 0.87–2.17 (21H, m), 3.07 (1H, dd, J=3.05 Hz, 6.38 Hz), 3.22 (1H, d, J=11.65 Hz), 3.45 (1H, dd, J=4.44 Hz, 9.44 Hz), 4.05 (1H, d, J=11.65 Hz), 4.32 (1H, d, J=11.65 Hz), 4.61 (1H, d, J=11.65 Hz), 5.24 (1H, t-like), 7.23–7.37 (5H, m).

MS EI (m/z): 588 (M$^+$)

Example 24

22β-Benzyloxyolean-12-ene-3β,24(4β)-diol (Compound 31)

Compound 30 (34 mg) was dissolved in a mixed solvent of 2 ml of methanol and 1 ml of dichloromethane, 0.5 ml of 1 N hydrochloric acid was added to the solution, and the mixture was stirred at room temperature for 30 min. After saturated sodium hydrogencarbonate was added to the reaction mixture, the mixture was extracted twice with dichloromethane. The organic layer was dried over magnesium sulfate. After the inorganic salt was removed by filtration, the filtrate was concentrated under reduced pressure to give 28 mg (yield 86%) of compound 31 as a colorless solid.

NMR (CDCl$_3$) δ ppm 0.89 (6H, s), 0.93 (3H, s), 0.94 (3H, s), 1.04 (3H, s), 1.11 (3H, s), 1.25 (3H, s), 0.83– 2.18 (21H, m), 2.38 (1H, brs), 2.69 (1H, brs), 3.07 (1H, d, J=3.08 Hz, 6.16 Hz), 3.32–3.36 (1H, m), 3.43–3.46 (1H, m), 4.20 (1H, d, J=10.51 Hz), 4.32 (1H, d, J=11.80 z), 4.61 (1H, d, J=11.80 Hz), 5.22 (1H, t-like), 7.23–7.38 (5H, m).

MS EI (m/z): 548 (M$^+$)

Example 25

22β-Ethoxy-3β,24(4β)-isopropylidenedioxyolean-12-ene (Compound 32)

The procedure of Example 23 was repeated, except that 100 mg of compound 1 and 80 μl of ethyl iodide were used as the starting compounds. Thus, 61 mg (yield 58%) of compound 32 was prepared as a colorless foam substance.

NMR (CDCl$_3$) δ ppm 0.87 (3H, s), 0.89 (3H, s), 0.99 (3H, s), 1.01 (3H, s), 1.12 (3H, s), 1.13 (3H, t, J=7.18 Hz), 1.15 (3H, s), 1.22 (3H, s), 1.37 (3H, s), 1.44 (3H, s), 0.90–2.11 (21H, m), 2.89 (1H, dd, J=2.82 Hz, 6.42 Hz), 3.23 (1H, d, J=11.28 Hz), 3.22–3.30 (1H, m), 3.46 (1H, dd, J=4.36 Hz, 9.24 Hz), 3.52–3.60 (1H, m), 4.05 (1H, d, J=11.28 Hz), 5.23 (1H, t-like).

MS EI (m/z): 526 (M$^+$)

Example 26

22β-Ethoxyolean-12-ene-3β,24(4β)-diol (Compound 33)

The procedure of Example 24 was repeated, except that 61 mg of compound 32 was used as the starting compound. Thus, 49 mg (yield 88%) of compound 33 was prepared as a colorless solid.

NMR (CDCl$_3$) δ ppm 0.86 (3H, s), 0.89 (3H, s), 0.90 (3H, s), 0.95 (3H, s), 1.01 (3H, s), 1.12 (3H, s), 1.14 (3H, t, J=7.22 Hz), 1.25 (3H, s), 0.84–2.13 (21H, m), 2.40 (1H, d, J=4.16 Hz), 2.70 (1H, d, J=8.87 Hz), 2.89 (1H, dd, J=2.77 Hz, 6.38 Hz), 3.22–3.30 (1H, m), 3.35 (1H, t, J=9.71 Hz), 3.42–3.47 (1H, m), 3.52–3.60 (1H, m), 4.21 (1H, d, J=9.71 Hz), 5.21 (1H, t-like).

MS EI (m/z): 486 (M$^+$)

Example 27

22β-Allyloxy-3β,24(4β)-isopropylidenedioxyolean-12-ene (Compound 34)

The procedure of Example 23 was repeated, except that 50 mg of compound 1 and 46 μl of allyl iodide were used as the starting compounds. Thus, 35 mg (yield 65%) of compound 34 was prepared as a colorless solid.

NMR (CDCl$_3$) δ ppm 0.89 (6H, s), 0.99 (3H, s), 1.01 (3H, s), 1.12 (3H, s), 1.16 (3H, s), 1.22 (3H, s), 1.37 (3H, s), 1.44 (3H, s), 0.87–2.15 (21H, m), 2.98 (1H, dd, J=2.78 Hz, 6.38 Hz), 3.23 (1H, d, J=11.65 Hz), 3.45 (1H, d, J=4.44 Hz, 9.43 Hz), 3.77–3.82 (1H, m), 4.02–4.07 (2H, m), 5.08–5.12 (1H, m),5.22–5.28 (2H, m), 5.85–5.93 (1H, m).

MS EI (m/z): 538 (M$^+$)

Example 28

22β-Allyloxyolean-12-ene-3β,24(4β)-diol (Compound 35)

The procedure of Example 24 was repeated, except that 33 mg of compound 34 was used as the starting compound. Thus, 27 mg (yield 88%) of compound 35 was prepared as a colorless solid.

NMR (CDCl$_3$) δ ppm 0.88 (3H, s), 0.89 (3H, s), 0.90 (3H, s), 0.94 (3H, s), 1.01 (3H, s), 1.11 (3H, s), 1.25 (3H, s), 0.84–2.75 (23H, m), 2.97–2.99 (1H, m), 3.32–3.38 (1H, m), 3.42–3.48 (1H, m), 3.77–3.83 (1H, m), 4.02–4.08 (1H, m), 4.21 (1H, d, J=11.09 Hz), 5.09–5.13 (1H, m), 5.21–5.28 (2H, m), 5.86–5.94 (1H, m).

MS EI (m/z): 498 (M+)

Example 29

22β-Benzoyloxy-3β,24(4β)-isopropylidenedioxyolean-12-ene (Compound 36)

Compound 1 (50 mg) was dissolved in 5 ml of dichloromethane, 18 mg of 4-dimethylaminopyridine and 17 μl of benzoyl chloride were added to the solution, and the mixture was then refluxed overnight. The reaction mixture was diluted with dichloromethane, washed with water, and dried over magnesium sulfate. After the inorganic salt was removed by filtration, the filtrate was concentrated under reduced pressure. The residue was purified by column chromatography on silica gel (n-hexane:ethyl acetate=3:1) to give 24 mg (yield 40%) of compound 36 as a colorless solid.

NMR (CDCl$_3$) δ ppm 0.91 (3H, s), 0.93 (3H, s), 1.00 (3H, s), 1.06 (3H, s), 1.16 (3H, s), 1.18 (3H, s), 1.23 (3H, s), 1.38 (3H, s), 1.44 (3H, s), 0.88–2.37 (21H, m), 3.23 (1H, d, J=11.54 Hz), 3.47 (1H, dd, J=4.44 Hz, 9.48 Hz), 4.05 (1H, d, J=11.54 Hz), 4.93 (1H, t, J=3.85 Hz), 5.33 (1H, t-like), 7.45 (2H, t, J=6.70 Hz), 7.55 (1H, t, J=6.70 Hz), 8.05 (2H, d, J=6.70 Hz).

MS EI (m/z): 602 (M+)

Example 30

22β-Benzoyloxyolean-12-ene-3β,24(4β)-diol (Compound 37)

The procedure of Example 24 was repeated, except that 24 mg of compound 36 was used as the starting compound. Thus, 19 mg (yield 83%) of compound 37 was prepared as a colorless solid.

NMR (CDCl$_3$) δ ppm 0.83 (3H, s), 0.84 (3H, s), 0.86 (3H, s), 0.88 (3H, s), 0.98 (3H, s), 1.11 (3H, s), 1.18 (3H, s), 0.78–2.78 (23H, m), 3.28 (1H, t, J=10.77 Hz), 3.35–3.40 (1H, m), 4.14 (1H, d, J=10.77 Hz), 4.86 (1H, t-like), 5.25 (1H, t-like), 7.37 (2H, t, J=7.18 Hz), 7.48 (1H, t, J=7.18 Hz), 7.98 (2H, d, J=7.18 Hz).

MS EI (m/z): 562 (M+)

Example 31

3β,24(4β)-Isopropylidenedioxy-22β-propionyloxyolean-12-ene (Compound 38)

The procedure of Example 29 was repeated, except that 100 mg of compound 1 and 27 μl of propionyl chloride were used as the starting compounds. Thus, 73 mg (yield 66%) of compound 38 was prepared as a colorless solid.

NMR (CDCl$_3$) δ ppm 0.82 (3H, s), 0.90 (3H, s), 0.99 (3H, s), 1.00 (3H, s), 1.44 (3H, t, J=7.69 Hz), 1.15 (3H, s), 1.16 (3H, s), 1.23 (3H, s), 1.38 (3H, s), 1.44 (3H, s), 0.88–2.23 (21H, m), 2.31 (2H, dq, J=3.34 Hz, 7.69 Hz), 3.24 (1H, d, J=11.54 Hz), 3.46 (1H, dd, J=4.36 Hz, 9.23 Hz), 4.05 (1H, d, J=11.54 Hz), 4.66 (1H, t, J=3.59 Hz), 5.27 (1H, t-like).

MS EI (m/z): 554 (M+)

Example 32

22β-Propionyloxyolean-12-ene-3β,24(4β)-diol (Compound 39)

The procedure of Example 24 was repeated, except that 73 mg of compound 38 was used as the starting compound. Thus, 56 mg (yield 82%) of compound 39 was prepared as a colorless solid.

NMR (CDCl$_3$) δ ppm 0.81 (3H, s), 0.89 (6H, s), 0.95 (3H, s), 1.00 (3H, s), 1.14 (3H, t, J=7.49 Hz), 1.15 (3H, s), 1.25 (3H, s), 0.84–2.75 (25H, m), 3.32–3.37 (1H, m), 3.43–3.46 (1H, m), 4.21 (1H, d, J=11.10 Hz), 4.66 (1H, t, J=2.89 Hz), 5.26 (1H, t-like).

MS EI (m/z): 514 (M+)

Example 33

3β,24(4β)-Isopropylidenedioxy-22β-valeryloxyolean-12-ene (Compound 40)

The procedure of Example 29 was repeated, except that 50 mg of compound 1 and 36 μl of valeryl chloride were used as the starting compounds. Thus, 32 mg (yield 55%) of compound 40 was prepared as a colorless solid.

NMR (CDCl$_3$) δ ppm 0.82 (3H, s), 0.90 (3H, s), 0.92 (3H, t, J=7.21 Hz), 0.99 (3H, s), 1.00 (3H, s), 1.15 (3H, s), 1.16 (3H, s), 1.23 (3H, s), 1.38 (3H, s), 1.44 (3H, s), 0.78–2.33 (27H, m), 3.23 (1H, d, J=11.65 Hz), 3.46 (1H, dd, J=4.44 Hz, 9.43 Hz), 4.06 (1H, d, J=11.65 Hz), 4.66 (1H, t, J=3.88 Hz), 5.28 (1H, t-like).

MS EI (m/z): 582 (M+)

Example 34

22β-Valeryloxyolean-12-ene-3β,24(4β)-diol (Compound 41)

The procedure of Example 24 was repeated, except that 31 mg of compound 40 were used as the starting compound. Thus, 17 mg (yield 59%) of compound 41 was prepared as a colorless solid.

NMR (CDCl$_3$) δ ppm 0.81 (3H, s), 0.89 (6H, s), 0.92 (3H, t, J=7.21 Hz), 0.95 (3H, s), 1.00 (3H, s), 1.15 (3H, s), 1.25 (3H, s), 0.84–2.71 (29H, m), 3.31–3.38 (1H, m), 3.42–3.49 (1H, m), 4.21 (1H, d, J=10.82 Hz), 4.66 (1H, t, J=3.61 Hz), 5.26 (1H, t-like).

MS EI (m/z): 542 (M+)

Example 35

22β-Trans-crotonyloxy-3β,24(4β)-isopropylidenedioxyolean-12-ene (Compound 42)

The procedure of Example 29 was repeated, except that 50 mg of compound 1 and 30 μl of trans-crotonyl chloride were used as the starting compounds. Thus, 9 mg (yield 16%) of compound 42 was prepared as a colorless solid.

NMR (CDCl$_3$) δ ppm 0.82 (3H, s), 0.90 (3H, s), 0.99 (3H, s), 1.00 (3H, s), 1.15 (6H, s), 1.23 (3H, s), 1.38 (3H, s), 1.44 (3H, s), 0.88–2.25 (24H, m), 3.23 (1H, d, J=11.65 Hz), 3.47 (1H, dd, J=4.44 Hz, 9.44 Hz), 4.05 (1H, d, J=11.65 Hz), 4.71 (1H, t, J=3.61 Hz), 5.28 (1H, t-like), 5.81–5.86 (1H, m), 6.90–6.99 (1H, m).

MS EI (m/z): 566 (M+)

Example 36

22β-Trans-crotonyloxyolean-12-ene-3β,24(4β)-diol (Compound 43)

The procedure of Example 24 was repeated, except that 9 mg of compound 42 was used as the starting compound. Thus, 5 mg (yield 59%) of compound 43 was prepared as a colorless solid.

NMR (CDCl$_3$) δ ppm 0.81 (3H, s), 0.89 (6H, s), 0.94 (3H, s), 0.99 (3H, s), 1.15 (3H, s), 1.25 (3H, s), 0.84–2.74 (26H, m), 3.31–3.38 (1H, m), 3.42–3.47 (1H, m), 4.20 (1H, d, J=10.77 Hz), 4.71 (1H, t, J=3.59 Hz), 5.26 (1H, t-like), 5.81–5.85 (1H, m), 6.89–6.98 (1H, m).

MS EI (m/z): 526 (M$^+$)

Example 37

22β-Cinnamoyloxy-3β,24(4β)-isopropylidenedioxyolean-12-ene (Compound 44)

The procedure of Example 29 was repeated, except that 50 mg of compound 1 and 50 mg of cinnamoyl chloride were used as the starting compounds. Thus, 39 mg (yield 63%) of compound 44 was prepared as a colorless solid.

NMR (CDCl$_3$) δ ppm 0.88 (3H, s), 0.92 (3H, s), 1.00 (3H, s), 1.05 (3H, s), 1.16 (3H, s), 1.17 (3H, s), 1.23 (3H, s), 1.38 (3H, s), 1.44 (3H, s), 0.90–2.32 (21H, m), 3.24 (1H, d, J=11.54 Hz), 3.47 (1H, dd, J=4.36 Hz, 9.23 Hz), 4.05 (1H, d, J=11.54 Hz), 4.80 (1H, t, J=3.59 Hz), 5.31 (1H, t-like), 6.43 (1H, d, J=15.90 Hz), 7.37–7.40 (3H, m), 7.52–7.55 (2H, m), 7.66 (1H, d, J=15.90 Hz).

MS EI (m/z): 628 (M$^+$)

Example 38

22β-Cinnamoyloxyolean-12-ene-3β,24(4β)-diol (Compound 45)

The procedure of Example 24 was repeated, except that 30 mg of compound 44 was used as the starting compound. Thus, 23 mg (yield 84%) of compound 45 was prepared as a colorless solid.

NMR (CDCl$_3$) δ ppm 0.87 (3H, s), 0.89 (3H, s), 0.91 (3H, s), 0.95 (3H, s), 1.04 (3H, s), 1.16 (3H, s), 1.25 (3H, s), 0.85–2.70 (23H, m), 3.31–3.38 (1H, m), 3.42–3.49 (1H, m), 4.21 (1H, d, J=11.02 Hz), 4.79 (1H, t-like), 5.29 (1H, t-like), 6.42 (1H, d, J=15.90 Hz), 7.36–7.40 (3H, m), 7.51–7.55 (2H, m), 7.65 (1H, d, J=15.90 Hz).

MS EI (m/z): 588 (M$^+$)

Example 39

3β,22β-Dibenzyloxy-24(4β)-N-methylamino-olean-12-ene (Compound 46)

Compound 7 (50 mg) was dissolved in a mixed solvent of 2 ml of methanol and 2 ml of dichloromethane, 0.1 ml of a 40% aqueous methylamine solution and 10 mg of 20% Pd(OH)$_2$—C were added to the solution. The mixture was then subjected to catalytic reduction under atmospheric pressure for 2 hr. After the reaction mixture was filtered through Celite, the filtrate was concentrated under reduced pressure. The residue was purified by column chromatography on silica gel (dichloromethane:methanol=5:1) to give 13 mg (yield 25%) of compound 46 as a colorless solid.

NMR (CDCl$_3$) δ ppm 0.89 (3H, s), 0.90 (3H, s), 0.93 (3H, s), 0.94(3H, s), 1.04 (3H, s), 1.10 (3H, s), 1.42 (3H, s), 0.87–2.19 (22H, m), 2.58 (3H, s), 3.00 (1H, d, J=12.20 Hz), 3.06–3.09 (1H, m), 3.15 (1H, d, J=12.20 Hz), 3.24–3.28 (1H, m), 4.32 (1H, d, J=11.65 Hz), 4.41 (1H, d, J=10.82 Hz), 4.61 (1H, d, J=11.65 Hz), 4.68 (1H, d, J=10.82 Hz), 5.21 (1H, t-like), 7.28–7.40 (10H, m).

MS TSP (m/z): 652 (M$^+$+1)

Example 40

24(4β)-N-Methylamino-olean-12-ene-3β,22β-diol (Compound 47)

Compound 46 (13 mg) was dissolved in a mixed solvent of 1 ml of methanol and 1 ml of dichloromethane, 10 mg of 20% Pd(OH)$_2$—C was added to the solution. The mixture was then subjected to catalytic reduction under atmospheric pressure for 5 hr. After the reaction mixture was filtered through Celite, the filtrate was concentrated under reduced pressure to give 4 mg (yield 49%) of compound 47 as a colorless solid.

NMR (CDCl$_3$) δ ppm 0.86 (3H, S), 0.92 (6H, s), 0.95 (3H, s), 1.03 (3H, s), 1.10 (3H, s), 1.33 (3H, s), 0.88–2.10 (23H, m), 2.68 (3H, s), 2.90 (1H, d, J 12.57 Hz), 3.18 (1H, d, J=12.57 Hz), 3.39–3.45 (3H, m), 5.25 (1H, t-like).

MS TSP (m/z): 472 (M$^+$+1)

Example 41

3β,24(4β)-Benzylidenedioxyolean-12-ene (Compound 48)

Compound 23 (500 mg) was dissolved in 12 ml of anhydrous DMF, 0.2 ml of benzaldehydediacetoacetal and a catalytic amount of camphorsulfonic acid were added to the solution. The mixture was then stirred at 45° C. overnight. Benzaldehydedimethylacetal (0.1 ml) was further added thereto, and the mixture was stirred at 45° C. for 8 hr. The reaction mixture was diluted with ethyl acetate, washed with saturated sodium hydrogencarbonate, and dried over magnesium sulfate. After the inorganic salt was removed by filtration, the filtrate was concentrated under reduced pressure. The residue was purified by column chromatography on silica gel (n-hexane:ethyl acetate=10:1) to give 498 mg (yield 83%) of compound 48 as a colorless solid.

NMR (CDCl$_3$) δ ppm 0.84 (3H, s), 0.88 (6H, s), 0.97 (3H, s), 1.07 (3H, s), 1.15 (3H, s), 1.48 (3H, s), 0.79–2.48 (23H, m), 3.60–3.67 (2H, m), 4.30 (1H, d, J=11.54 Hz), 5.19 (1H, t-like), 5.78 (1H, s), 7.30–7.52 (5H, m).

MS TSP (m/z): 531 (M$^+$+1)

Example 42

3β-Benzyloxyolean-12-en-24(4β)-ol (Compound 49) and 24(4β)-benzyloxyolean-12-en-3β-ol (Compound 50)

Compound 48 (200 mg) was dissolved in 3 ml of anhydrous toluene, and 1.5 ml of a solution of diisobutylaluminum hydride (1.0 M) in toluene was dropwise added to the solution at −25 to −20° C. The mixture was stirred for one hr, and further stirred for 3 hr while gradually returning the temperature of the mixture to room temperature. After water was added to the reaction mixture, the mixture was extracted with ethyl acetate. The organic layer was dried over magnesium sulfate. After the inorganic salt was removed by filtration, the solution was concentrated under reduced pressure. The residue was purified by column chromatography on silica gel (n-hexane:ethyl acetate=10:1) to give, as a colorless solid, 61 mg (yield 30%) of compound 49 and 96 mg (yield 48%) of compound 50.

Compound 49

NMR (CDCl$_3$) δ ppm 0.82 (3H, s), 0.87 (6H, s), 0.89 (3H, s), 0.94 (3H, s), 1.12 (3H, s), 1.21 (3H, s), 0.78–2.01 (23H, m), 3.17–3.28 (3H, m), 4.16 (1H, d, J=10.34 Hz), 4.40 (1H, d, J=11.38 Hz), 4.67 (1H, d, J=11.38 Hz), 5.18 (1H, t-like), 7.25–7.37 (5H, m).

MS FAB (m/z): 533 (M$^+$+1)

Compound 50:

NMR (CDCl$_3$) δ ppm 0.82 (3H, s), 0.85 (3H, s), 0.86 (3H, s), 0.87 (3H, s), 0.92 (3H, s), 1.12 (3H, s), 1.28 (3H, s), 0.80–2.01 (23H, m), 3.22–3.31 (2H, m), 3.94 (1H, d, J=7.21

Hz), 4.00 (1H, d, J=9.16 Hz), 4.48 (2H, d, J=2.77 Hz), 5.17 (1H, t-like), 7.26–7.37 (5H, m).

MS EI (m/z): 532 (M$^+$)

Example 43

24(4β)-Acetoxy-3β-benzyloxyolean-12-ene (Compound 51)

Compound 49 (16 mg) was dissolved in 0.5 ml of dichloromethane, 0.5 ml of pyridine and 0.5 ml of acetic anhydride were added to the solution, and the mixture was stirred at room temperature overnight. After ice water was added to the reaction mixture, the mixture was extracted with ethyl acetate. The extract was dried over magnesium sulfate. After the inorganic salt was removed by filtration, the filtrate was concentrated under reduced pressure. The residue was purified by column chromatography on silica gel (n-hexane:ethyl acetate=5:1) to give 14 mg (yield 81%) of compound 51 as a colorless solid.

NMR (CDCl$_3$) δ ppm 0.83 (3H, s), 0.87 (6H, s), 0.96 (3H, s), 0.97 (3H, s), 1.12 (3H, s), 1.15 (3H, s), 0.78–2.00 (23H, m), 1.98 (3H, s), 3.03 (1H, dd, J=4.16 Hz, 11.65 Hz), 4.19 (1H, d, J=11.93 Hz), 4.35 (1H, d, J=11.93 Hz), 4.37 (1H, d, J=11.65 Hz), 4.65 (1H, d, J=11.65 Hz), 5.19 (1H, t-like), 7.27–7.34 (5H, m).

MS EI (m/z): 574 (M$^+$)

Example 44

24(4β)-Acetoxyolean-12-en-3β-ol (Compound 52)

The procedure of Example 8 was repeated, except that 14 mg of compound 51 was used as the starting compound. Thus, 8 mg (yield 65%) of compound 52 was prepared as a colorless solid.

NMR (CDCl$_3$) δ ppm 0.83 (3H, s), 0.87 (6H, s), 0.93 (3H, s), 0.95 (3H, s), 1.13 (3H, s), 1.15 (3H, s), 0.78–2.08 (24H, m), 2.06 (3H, s), 3.30 (1H, dd, J=4.71 Hz, 11.38 Hz), 4.14 (1H, d, J=11.65 Hz), 4.35 (1H, d, J=11.65 Hz), 5.18 (1H, t-like).

MS EI (m/z): 484 (M$^+$)

Example 45

3β-Benzyloxy-24(4β)-methoxyolean-12-ene (Compound 53)

The procedure of Example 21 was repeated, except that 26 mg of compound 49 and 30 µl of methyl iodide was used as the starting compound. Thus, 17 mg (yield 61%) of compound 53 was prepared as a colorless solid.

NMR (CDCl$_3$) δ ppm 0.83 (3H, s), 0.87 (6H, s), 0.96(3H, s), 1.01 (3H, s), 1.12 (3H, s), 1.15 (3H, s), 0.75–2.00 (23H, m), 2.98 (1H, dd, J=4.10 Hz, 11.79 Hz), 3.27 (3H, s), 3.39 (1H, d, J=9.75 Hz), 3.65 (1H, d, J=9.75 Hz), 4.42 (1H, d, J=11.80 Hz), 4.63 (1H, d, J=11.80 Hz), 5.19 (1H, t-like), 7.25–7.36 (5H, m).

MS EI (m/z): 546 (M$^+$)

Example 46

24(4β)-Methoxyolean-12-en-3β-ol (Compound 54)

The procedure of Example 8 was repeated, except that 17 mg of compound 53 was used as the starting compound. Thus, 12 mg (yield 86%) of compound 54 was prepared as a colorless solid.

NMR (CDCl$_3$) δ ppm 0.82 (3H, s), 0.86 (3H, s), 0.87 (3H, s), 0.91 (3H, s), 0.94 (3H, s), 1.13 (3H, s), 1.22 (3H, s), 0.78–2.02 (23H, m), 3.21 (1H, d, J=9.16 Hz), 3.22–3.29 (1H, m), 3.31 (3H, s), 3.89 (1H, d, J=9.16 Hz), 3.91–3.95 (1H, m), 5.18 (1H, t-like).

MS EI (m/z): 456 (M$^+$)

Example 47

3β-Acetoxy-24(4β)-benzyloxyolean-12-ene (Compound 55)

The procedure of Example 43 was repeated, except that 25 mg of compound 50 was used as the starting compound. Thus, 21 mg (yield 79%) of compound 55 was prepared as a colorless solid.

NMR (CDCl$_3$) δ ppm 0.83 (3H, s), 0.87 (3H, s), 0.88 (3H, s), 0.95 (6H, s), 1.07 (3H, s), 1.12 (3H, s), 2.03 (3H, s), 0.78–2.00 (23H, m), 3.49 (1H, d, J=9.43 Hz), 3.73 (1H, d, J=9.43 Hz), 4.48 (2H, s), 4.57 (1H, dd, J=4.72 Hz, 11.10 Hz), 5.18 (1H, t-like), 7.25–7.35 (5H, m).

MS EI (m/z): 574 (M$^+$)

Example 48

3β-Acetoxyolean-12-en-24(4β)-ol (Compound 56)

The procedure of Example 8 was repeated, except that 21 mg of compound 55 was used as the starting compound. Thus, 10 mg (yield 56%) of compound 56 was prepared as a colorless solid.

NMR (CDCl$_3$) δ ppm 0.82 (3H, s), 0.87 (3H, s), 0.88 (3H, s), 0.91 (3H, s), 0.95 (3H, s), 1.09 (3H, s), 1.13 (3H, s), 0.79–2.00 (24H, m), 2.08 (3H, s), 3.37–3.43 (1H, m), 4.16 (1H, d, J=12.21 Hz), 4.65 (1H, t, J=8.05 Hz), 5.18 (1H, t-like).

MS EI (m/z): 484 (M$^+$)

Example 49

24(4β)-Benzyloxy-3β-methoxyolean-12-ene (Compound 57)

The procedure of Example 23 was repeated, except that 26 mg of compound 50 and 30 µl of methyl iodide were used as the starting compounds. Thus, 19 mg (yield 70%) of compound 57 was prepared as a colorless solid.

NMR (CDCl$_3$) δ ppm 0.83 (3H, s), 0.87 (6H, s), 0.94 (6H, s), 1.12 (3H, s), 1.17 (3H, s), 0.79–2.02 (23H, m), 2.72 (1H, dd, J=4.14 Hz, 11.93 Hz), 3.34 (3H, s), 3.39 (1H, d, J=9.71 Hz), 3.72 (1H, d, J=9.71 Hz), 4.44 (2H, s), 5.18 (1H, t-like), 7.22–7.35 (5H, m).

MS EI (m/z): 546 (M$^+$)

Example 50

3β-Methoxyolean-12-en-24(4β)-ol (Compound 58)

The procedure of Example 8 was repeated, except that 19 mg of compound 57 was used as the starting compound. Thus, 9 mg (yield 56%) of compound 58 was prepared as a colorless solid.

NMR (CDCl$_3$) δ ppm 0.82 (3H, s), 0.87 (9H, s), 0.94 (3H, s), 1.13 (3H, s), 1.20 (3H, s), 0.79–2.02 (23H, m), 2.93 (1H, dd, J=4.16 Hz, 11.38 Hz), 3.18–3.25 (2H, m), 3.36 (3H, s), 4.10–4.14 (1H, m), 5.18 (1H, t-like).

MS EI (m/z): 456 (M$^+$)

Example 51

24(4β)-Acetoxy-3β,22β-benzyloxyolean-12-ene (Compound 59)

The procedure of Example 43 was repeated, except that 30 mg of compound 6 was used as the starting compound.

Thus, 24 mg (yield 76%) of compound 59 was prepared as a colorless solid.

NMR (CDCl$_3$) δ ppm 0.89 (3H, s), 0.94 (3H, s), 0.96 (3H, s), 0.97 (3H, s), 1.05 (3H, s), 1.11 (3H, s), 1.15 (3H, s), 1.98 (3H, s), 0.84–2.18 (21H, m), 3.02 (1H, dd, J=4.16 Hz, 11.65 Hz), 3.07 (1H, dd, J=2.77 Hz, 6.10 Hz), 4.18 (1H, d, J=11.93 Hz), 4.32 (1H, d, J=11.93 Hz), 4.35 (1H, d, J=11.93 Hz), 4.37 (1H, d, J=11.93 Hz), 4.62 (1H, d, J=11.93 Hz), 4.65 (1H, d, J=11.93 Hz), 5.23 (1H, t-like), 7.23–7.36 (10H, m).

MS EI (m/z): 680 (M$^+$)

Example 52

24(4β)-Acetoxyolean-12-ene-3β,22β-diol (Compound 60)

The procedure of Example 8 was repeated, except that 24 mg of compound 59 was used as the starting compound. Thus, 12 mg (yield 69%) of compound 60 was prepared as a colorless solid.

NMR (CDC13) δ ppm 0.87 (3H, s), 0.91 (3H, s), 0.94 (3H, s), 0.96 (3H, s), 1.04 (3H, s), 1.12 (3H, s), 1.16 (3H, s), 0.84–2.12 (23H, m), 2.07 (3H, s), 3.27–3.31 (1H, m), 3.44 (1H, t, J=5.28 Hz), 4.14 (1H, d, J=11.66 Hz), 4.35 (1H, d, J=11.66 Hz), 5.25 (1H, t-like).

MS EI (m/z): 500 (M$^+$)

Example 53

3β,22β-Dibenzyloxy-24(4β)-propionyloxyolean-12-ene (Compound 61)

The procedure of Example 29 was repeated, except that 32 mg of compound 6 and 6.8 μl of propionyl chloride were used as the starting compounds. Thus, 22 mg (yield 62%) of compound 61 was prepared as a colorless solid.

NMR (CDCl$_3$) δ ppm 0.89 (3H, s), 0.94 (3H, s), 0.96 (3H, s), 0.97 (3H, s), 1.05 (3H, s), 1.09 (3H, t, J=7.49 Hz), 1.11 (3H, s), 1.15 (3H, s), 0.84–2.30 (23H, m), 3.00–3.10 (2H, m), 4.20 (1H, d, J=11.55 Hz), 4.30–4.39 (3H, m), 4.60–4.67 (2H, m), 5.23 (1H, t-like), 7.25–7.35 (10H, m).

MS EI (m/z): 694 (M$^+$)

Example 54

24(4β)-Propionyloxyolean-12-ene-3β,22β-diol (Compound 62)

The procedure of Example 8 was repeated, except that 21 mg of compound 61 was used as the starting compound. Thus, 14 mg (yield 88%) of compound 62 was prepared as a colorless solid.

NMR (CDCl$_3$) δ ppm 0.88 (3H, s), 0.92 (3H, s), 0.94 (3H, s), 0.97 (3H, s), 1.05 (3H, s), 1.12 (3H, s), 1.15 (3H, t, J=7.49 Hz), 1.16 (3H, s), 0.89–2.13 (22H, m), 2.35 (2H, q, J=7.49 Hz), 3.29 (1H, dd, J=4.72 Hz, 10.82 Hz), 3.42–3.45 (1H, m), 3.49 (1H, s), 4.16 (1H, d, J=11.66 Hz), 4.37 (1H, d, J=11.66 Hz), 5.26 (1H, t-like).

MS EI (m/z): 514 (M$^+$)

Example 55

3β,22β-Dibenzyloxy-24(4β)-methoxyolean-12-ene (Compound 63)

The procedure of Example 23 was repeated, except that 20 mg of compound 6 and 0.3 ml of methyl iodide were used as the starting compounds. Thus, 8 mg (yield 38%) of compound 63 was prepared as a colorless solid.

NMR (CDCl$_3$) δ ppm 0.89 (3H, s), 0.94 (3H, s), 0.97 (3H, s), 1.02 (3H, s), 1.04 (3H, s), 1.10 (3H, s), 1.15 (3H, s), 0.78–2.18 (21H, m), 2.95–3.00 (1H, m), 3.05–3.10 (1H, m), 3.27 (3H, s), 3.39 (1H, d, J=9.75 Hz), 3.65 (1H, d, J=9.75 Hz), 4.32 (1H, d, J=11.80 Hz), 4.42 (1H, d, J=11.80 Hz), 4.61 (1H, d, J=11.80 Hz), 4.63 (1H, d, J=11.80 Hz), 5.23 (1H, t-like), 7.24–7.35 (10H, m).

MS EI (m/z): 652 (M$^+$)

Example 56

24(4β)-Methoxyolean-12-ene-3β,22β-diol (Compound 64)

The procedure of Example 8 was repeated, except that 8 mg of compound 63 was used as the starting compound. Thus, 6 mg (yield 98%) of compound 64 was prepared as a colorless solid.

NMR (CDCl$_3$) δ ppm 0.87 (3H, s), 0.91 (3H, s), 0.92 (3H, s), 0.95 (3H, s), 1.04 (3H, s), 1.11 (3H, s), 1.22 (3H, s), 0.84–2.12 (23H, m), 3.20 (1H, d, J=9.15 Hz), 3.23–3.27 (1H, m), 3.31 (3H, s), 3.42–3.44 (1H, m), 3.89 (1H, d, J=9.15 Hz), 5.24 (1H, t-like).

MS EI (m/z): 472 (M$^+$)

Example 57

3β,24(4β)-Benzylidenedioxyolean-12-en-22β-ol (Compound 65)

The procedure of Example 41 was repeated, except that 1.00 g of compound 9 was used as the starting compound. Thus, 997 mg (yield 83%) of compound 65 was prepared as a colorless solid.

NMR (CDCl$_3$) δ ppm 0.88 (3H, s), 0.92 (3H, s), 0.99 (3H, s), 1.05 (3H, s), 1.08 (3H, s), 1.14 (3H, s), 1.48 (3H, s), 0.90–2.50 (22H, m), 3.44 (1H, q, J=5 Hz), 3.60–3.67 (2H, m), 4.30 (1H, d, J=11 Hz), 5.26 (1H, t-like), 5.78 (1H, s), 7.30–7.40 (3H, m), 7.45–7.55 (2H, m).

MS EI (m/z): 546 (M$^+$)

Example 58

22β-Benzyloxy-3β,24(4β)-benzylidenedioxyolean-12-ene (Compound 66)

The procedure of Example 23 was repeated, except that 5.42 g of compound 65 was used as the starting compound. Thus, 3.24 mg (yield 51%) of compound 66 was prepared as a colorless solid.

NMR (CDCl$_3$) δ ppm 0.90 (3H, s), 0.95 (3H, s), 0.98 (3H, s), 1.05 (3H, s), 1.07 (3H, s), 1.13 (3H, s), 1.48 (3H, s), 0.90–2.50 (21H, m), 3.08 (1H, q, J=3 Hz), 3.60–3.66 (2H, m), 4.30 (1H, d, J=11Hz), 4.32 (1H, d, J=12 Hz), 4.60 (1H, t, J=11 Hz), 5.24 (1H, t-like), 5.78 (1H, s), 7.2–7.6 (10H, m).

MS EI (m/z): 636 (M$^+$)

Example 59

22β,24(4β)-Dibenzyloxyolean-12-en-3β-ol (Compound 67)

The procedure of Example 42 was repeated, except that 400 g of compound 66 was used as the starting compound. Thus, 275 mg (yield 69%) of compound 67 and 25.1 mg (yield 6%) of compound 6 were prepared as a colorless solid.

NMR (CDCl$_3$) δ ppm 0.85 (3H, s), 0.89 (3H, s), 0.93 (6H, s), 1.04 (3H, s), 1.11 (3H, s), 1.28 (3H, s), 0.80–2.20 (22H, m), 3.05–3.08 (1H, m), 3.26–3.30 (2H, m), 3.95–4.02 (1H, m), 4.31 (1H, d, J=12 Hz), 4.48 (2H, s), 4.61 (1H, d, J=12 Hz), 5.21 (1H, t-like), 7.26–7.33 (10H, m).

MS EI (m/z): 639 (M$^+$)

Example 60

3β-Acetoxy-22β,24(4β)-dibenzyloxyolean-12-ene (Compound 68)

The procedure of Example 43 was repeated, except that 100 g of compound 67 was used as the starting compound. Thus, 33 mg (yield 30%) of compound 68 was prepared as a colorless solid.

NMR (CDCl$_3$) δ ppm 0.89 (3H, s), 0.93 (3H, s), 0.95 (6H, s), 1.04 (3H, s), 1.06 (3H, s), 1.10 (3H, s), 2.02 (3H, s), 0.90–2.18 (21H, m), 3.05–3.09 (1H, m), 3.48 (1H, d, J=9.71 Hz), 3.73 (1H, d, J=9.71 Hz), 4.32 (1H, d, J=11.65 Hz), 4.47 (2H, s), 4.57 (1H, dd, J=4.71 Hz, 11.37 Hz), 4.61 (1H, d, J=11.65 Hz), 5.22 (1H, t-like), 7.25–7.36 (10H, m).

MS EI (m/z): 680 (M$^+$)

Example 61

3β-Acetoxyolean-12-ene-22β,24(4β)-diol (Compound 69)

The procedure of Example 8 was repeated, except that 32 mg of compound 68 was used as the starting compound. Thus, 15 mg (yield 64%) of compound 69 was prepared as a colorless solid.

NMR (CDCl$_3$) δ ppm 0.87 (3H, s), 0.91 (3H, s), 0.92 (3H, s), 0.96 (3H, s), 1.04 (3H, s), 1.09 (3H, s), 1.11 (3H,s), 2.08 (3H, s), 0.90–2.12 (23H, m), 3.37–3.46 (2H, m), 4.15 (1H, d, J=11.80 Hz), 4.62–4.67 (1H, m), 5.25 (1H, t-like).

MS EI (m/z): 500 (M$^+$)

Example 62

22β,24(4β)-Dibenzyloxy-3β-methoxyolean-12-ene (Compound 70)

The procedure of Example 23 was repeated, except that 100 mg of compound 67 was used as the starting compound. Thus, 49 mg (yield 47%) of compound 70 was prepared as a colorless solid.

NMR (CDCl$_3$) δ ppm 0.89 (3H, s), 0.93 (3H, s), 0.94 (3H, s), 0.95 (3H, s), 1.04 (3H, s), 1.10 (3H, s), 1.17 (3H, s), 0.75–2.17 (21H, m), 2.73 (1H, dd, J=4.11 Hz, 11.80 Hz), 3.05–3.08 (1H, m), 3.34 (3H, s), 3.38 (1H, d, J=9.75 Hz), 3.71 (1H, d, J=9.75 Hz), 4.32 (1H, d, J=12.05 Hz), 4.44 (2H, s), 4.61 (1H, d, J=12.05 Hz), 5.22 (1H, t-like), 7.23–7.36 (10H, m).

MS TSP (m/z): 653 (M$^+$+1)

Example 63

3β-Methoxyolean-12-ene-22β,24(4β)-diol (Compound 71)

The procedure of Example 8 was repeated, except that 48 mg of compound 70 was used as the starting compound. Thus, 21 mg (yield 59%) of compound 71 was prepared as a colorless solid.

NMR (CDCl$_3$) δ ppm 0.87 (3H, s), 0.88 (3H, s), 0.91 (3H, s), 0.95 (3H, s), 1.04 (3H, s), 1.11 (3H, s), 1.20 (3H, s), 0.84–2.14 (22H, m), 2.92 (1H, dd, J=4.71 Hz, 11.80 Hz), 3.19–3.24 (2H, m), 3.36 (3H, s), 3.44 (1H, t-like), 4.10–4.15 (1H, m), 5.25 (1H, t-like).

MS TSP (m/z): 473 (M$^+$+1)

Example 64

3β,22β-Dibenzyloxyolean-12-en-24(4β)-oic acid methyl ester (Compound 72)

Compound 10 (15 mg) was dissolved in 1 ml of methanol, and a solution of trimethylsilyldiazomethane in hexane was added to the solution until yellow color became not disappeared. After the reaction mixture was concentrated under reduced pressure, the residue was purified by column chromatography on silica gel (n-hexane:ethyl acetate=4:1) to give 13 mg (yield 83%) of compound 72 as a colorless foam substance.

NMR (CDCl$_3$) δ ppm 0.83 (3H, s), 0.89 (3H, s), 0.93 (3H, s), 0.95 (3H, s), 1.04 (3H, s), 1.09 (3H, s), 1.31 (3H, s), 0.85–2.32 (21H, m), 2.96 (1H, dd, J=4.16 Hz, 11.93 Hz), 3.07 (1H, dd, J=3.05 Hz, 6.38 Hz), 3.65 (3H, s), 4.32 (1H, d, J=11.93 Hz), 4.48 (1H, d, J=12.21 Hz), 4.61 (1H, d, J=11.93 Hz), 4.72 (1H, d, J=12.21 Hz), 5.22 (1H, t-like), 7.26–7.37 (10H, m).

MS FAB (m/z): 667 (M$^+$+l)

Example 65

3β,22β-Dihydroxyolean-12-en-24(4β)-oic acid methyl ester (Compound 73)

The procedure of Example 8 was repeated, except that 12 mg of compound 72 was used as the starting compound. Thus, 9 mg (yield 100%) of compound 73 was prepared as a colorless solid.

NMR (CDCl$_3$) δ ppm 0.80 (3H, s), 0.88 (3H, s), 0.92 (3H, s), 0.99 (3H, s), 1.04 (3H, s), 1.12 (3H, s), 1.42 (3H, s), 0.72–2.12 (21H, m), 3.07–3.13 (1H, m), 3.43–3.48 (1H, m), 3.69 (3H, s), 5.27 (1H, t-like).

MS EI (m/z): 486 (M$^+$)

The substituents in the formula (I-1) corresponding to the structures of the compounds 1 to 73 are as shown in Table 1.

TABLE 1

| COMPOUND NO. | R$^1$ | R$^2$ | R$^3(\alpha)$ | R$^4(\beta)$ |
|---|---|---|---|---|
| 1 | —OC(CH$_3$)$_2$OCH$_2$— | | H | OH |
| 2 | OH | CH$_2$OH | =O | |
| 3 | OH | CH$_2$OH | Me | OH |
| 4 | OH | CH$_2$OTr | H | OH |
| 5 | OBn | CH$_2$OTr | H | OBn |
| 6 | OBn | CH$_2$OH | H | OBn |
| 7 | OBn | CHO | H | OBn |
| 8 | OH | CHO | H | OH |
| 9 | OH | CH$_2$OH | H | OH |
| 10 | OBn | COOH | H | OBn |
| 11 | OH | COOH | H | OH |
| 12 | OH | CH$_2$OH | =CH$_2$ | |
| 13 | OH | CH$_2$OH | Me | H |
| 14 | OH | CH$_2$OH | H | CH$_2$OH |
| 15 | —OC(CH$_3$)$_2$OCH$_2$— | | H | CH$_2$OH |
| 16 | —OC(CH$_3$)$_2$OCH$_2$— | | H | CHO |
| 17 | OH | CH$_2$OH | H | CHO |
| 18 | —OC(CH$_3$)$_2$OCH$_2$— | | H | COOH |
| 19 | OH | CH$_2$OH | H | COOH |
| 20 | —OC(CH$_3$)$_2$OCH$_2$— | | H | OTs |
| 21 | —OC(CH$_3$)$_2$OCH$_2$— | | H | — |
| 22 | OH | CH$_2$OH | H | — |
| 23 | OH | CH$_2$OH | H | H |
| 24 | —OC(CH$_3$)$_2$OCH$_2$— | | H | OAc |
| 25 | OH | CH$_2$OH | H | OAc |
| 26 | —OC(CH$_3$)$_2$OCH$_2$— | | H | OMe |
| 27 | OH | CH$_2$OH | H | OMe |
| 28 | OH | Me | H | OH |
| 29 | OMe | CH$_2$OMe | H | OMe |
| 30 | —OC(CH$_3$)$_2$OCH$_2$— | | H | OBn |
| 31 | OH | CH$_2$OH | H | OBn |
| 32 | —OC(CH$_3$)$_2$CH$_2$— | | H | OEt |
| 33 | OH | CH$_2$OH | H | OEt |
| 34 | —OC(CH$_3$)$_2$CH$_2$— | | H | OCH$_2$CH=CH$_2$ |
| 35 | OH | CH$_2$OH | H | OCH$_2$CH=CH$_2$ |
| 36 | —OC(CH$_3$)$_2$OCH$_2$— | | H | OCCPh |
| 37 | OH | CH$_2$OH | H | OCCPh |
| 38 | —OC(CH$_3$)$_2$OCH$_2$— | | H | OCOEt |
| 39 | OH | CH$_2$OH | H | OCOEt |
| 40 | —OC(CH$_3$)$_2$OCH$_2$— | | H | OCO$^n$Bu |
| 41 | OH | CH$_2$OH | H | OCO$^n$Bu |
| 42 | —OC(CH$_3$)$_2$OCH$_2$— | | H | OCOCH=CHCH$_3$ |
| 43 | OH | CH$_2$OH | H | OCOCH=CHCH$_3$ |
| 44 | —OC(CH$_3$)$_2$OCH$_2$— | | H | OCOCH—CHPh |
| 45 | OH | CH$_2$OH | H | OCOCH—CHPh |
| 46 | OBn | CH$_2$NHCH$_3$ | H | OBn |
| 47 | OH | CH$_2$NHCH$_3$ | H | OH |
| 48 | —OCH(Ph)OCH$_2$— | | H | H |
| 49 | OBn | CH$_2$OH | H | H |
| 50 | OH | CH$_2$OBn | H | H |
| 51 | OBn | CH$_2$OAc | H | H |
| 52 | OH | CH$_2$OAc | H | H |
| 53 | OBn | CH$_2$OMe | H | H |
| 54 | OH | CH$_2$OMe | H | H |
| 55 | OAc | CH$_2$OBn | H | H |
| 56 | OAc | OH$_2$OH | H | H |
| 57 | OCH$_3$ | CH$_2$OBn | H | H |
| 58 | OCH$_3$ | CH$_2$OH | H | H |
| 59 | OBn | CH$_2$OAc | H | OBn |
| 60 | OH | CH$_2$OAc | H | OH |
| 61 | OBn | CH$_2$OCOEt | H | OBn |
| 62 | OH | CH$_2$OCOEt | H | OH |
| 63 | OBn | CH$_2$OMe | H | OBn |
| 64 | OH | CH$_2$OMe | H | OH |
| 65 | —OCH(Ph)OCH$_2$— | | H | OH |
| 66 | —OCH(Ph)OCH$_2$— | | H | OBn |
| 67 | OH | CH$_2$OBn | H | OBn |
| 68 | OAc | CH$_2$OBn | H | OBn |
| 69 | OAc | CH$_2$OH | H | OH |
| 70 | OCH$_3$ | CH$_2$OBn | H | OBn |
| 71 | OCH$_3$ | CH$_2$OH | H | OH |
| 72 | OBn | COOMe | H | OBn |
| 73 | OH | COOMe | H | OH |

In the table,

Tr represents a trityl group, Bn a benzyl group, and Ts a tosyl group.

In the the compounds 1 to 20 and 23 to 73, — — — represents a single bond. On the other hand, in the compounds 21 and 22, — — — represents a double bond.

PREPARATION EXAMPLE 1

Tablets

The compound of the present invention was granulated by the wet process. After magnesium stearate was added thereto, the mixture was compressed to prepare tablets. Each tablet had the following composition.

| | |
|---|---|
| Compound 9 | 200 mg |
| Lactose | 50 mg |
| Carboxymethyl starch sodium | 20 mg |
| Hydroxypropylmethyl cellulose | 5 mg |
| Magnesium stearate | 3 mg |
| Total | 278 mg |

PREPARATION EXAMPLE 2

Suppositories

Weilapzole H-15 was heated at 60° C., and the compound 9 was added to and dispersed in the resultant melt. The dispersion was filled into suppository containers. The suppository containers were then cooled to room temperature to prepare suppositories. Each suppository had the following composition.

| | |
|---|---|
| Compound 9 | 200 mg |
| Weilapzole H-15 | 1000 mg |
| Total | 1200 mg |

TEST EXAMPLE 1

Study With Hepatocytotoxicity Inhibitory Model (In Vitro)

A test compound was added to a concentration of 0.1 to 10 μg/ml to Hep G2 cells in the presence of aflatoxin $B_1$ ($10^{-5}$ M). The cells were then incubated in a $CO_2$ incubator at 37° C. for 48 hr. After the incubation, the cells were dyed with trypan blue. The dye incorporation capacity thereof was measured with Monocellater (manufactured by Olympus Optical Co., Ltd.). The hepatocytotoxicity inhibitory activity (%) was calculated according to the following equation. In the equation, the value of the control group is the absorbance (%) in the presence of aflatoxin $B_1$ alone, and the value of the treated group is the absorbance (%) in the copresence of aflatoxin $B_1$ and the test compound.

As a result, the hepatocytotoxicity inhibitory activity of the compounds 1, 3, 8, 9, 10, 11, 14, 19, 23, 25, 27, 35, 37, 43, 45, 52, 54, 60, 64, 71, and 73 was more than 5%.

$$\text{Hepatocytotoxicity inhibitory activity (\%)} = \frac{\text{value of control group} - \text{value of treated group}}{100 - \text{value of control group}} \times 100$$

Acute Toxicity

The compound 9 of the present invention was intravenously administered to a C3H male mouse at a dose of 4 mg/kg, twice a day for 3 days. As a result, there is no significant toxicity.

What is claimed is:

1. A triterpene derivative represented by the formula (II) or a pharmaceutically acceptable salt thereof:

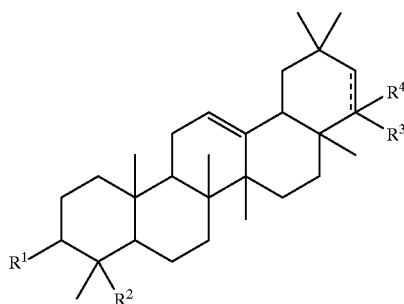

wherein $R^1$ represents a hydroxyl group,
  $C_{1-6}$ alkoxy,
  $C_{1-6}$ alkylcarbonyloxy, or
  aralkyloxy which may be optionally substituted;

$R^2$ represents $C_{1-6}$ alkyl,
  —$CH_2OR^5$ wherein $R^5$ represents a hydrogen atom, $C_{1-6}$ alkyl, aralkyl which may be optionally substituted, or $C_{1-6}$ alkylcarbonyl,
  formyl,
  —$COOR^6$ wherein $R^6$ represents a hydrogen atom or $C_{1-6}$ alkyl), or
  —$CH_2N(R^7)R^8$ wherein $R^7$ and $R^8$, which may be the same or different, represent a hydrogen atom or $C_{1-6}$ alkyl; or $R^1$ and $R^2$ may combine with each other to form —O—$CR^9(R^{10})$—$OCH_2$— wherein $R^9$ and $R^{10}$, which may be the same or different, represent a hydrogen atom, a $C_{1-6}$ alkyl group, or an aryl group;

$R^3$ and $R^4$, which may be the same or different, represent
  $C_{1-6}$ alkyl,
  hydroxy $C_{1-6}$ alkyl,
  formyl,
  —$COOR^{11}$ wherein $R^{11}$ represents a hydrogen atom or $C_{1-6}$ alkyl, or
  —$OR^{12}$ wherein $R^{12}$ represents $C_{1-6}$ alkyl, aralkyl which may be optionally substituted, arylcarbonyl, $C_{2-6}$ alkenyl, $C_{2-6}$ alkenylcarbonyl, or arylalkenylcarbonyl which may be optionally substituted; or $R^3$ and $R^4$ may combine with each other to form a methylene group;

— — — represents a single or double bond, provided that, when — — — represents a double bond, $R^4$ is absent;

when $R^1$ and $R^2$ combine with each other to form —O—$CR^9(R^{10})$—$OCH_2$— wherein any one of $R^9$ and $R^{10}$ represents aryl, $R^3$ and $R^4$ may further represent a hydrogen atom or a hydroxyl group;

when any one of $R^3$ and $R^4$ represents a $C_{1-6}$ alkyl group, the other substituent may further represent a hydroxyl group.

2. The compound according to claim 1, wherein $R^1$ represents a hydroxyl group and $R^2$ represents $CH_2OR^5$.

3. The compound according to claim 2, wherein $R^5$ represents a hydrogen atom and $R^4$ represents —$OR^{12}$ wherein $R^{12}$ represents $C_{1-6}$ alkyl, aralkyl which may be optionally substituted, arylcarbonyl which may be optionally substituted, $C_{2-6}$ alkenyl, $C_{2-6}$ alkenylcarbonyl, or arylalkenylcarbonyl which may be optionally substituted.

4. The compound according to claim 1, wherein $R^1$ and $R^2$ combine with each other to form —O—$CR^9(R^{10})$—$OCH_2$.

5. The compound according to claim 4, wherein $R^9$ and $R^{10}$ represent methyl, $R^3$ represents a hydrogen atom and $R^4$ represents —$OR^{12}$ wherein $R^{12}$ represents $C_{1-6}$ alkyl, arylcarbonyl which may be optionally substituted, $C_{2-6}$ alkenyl, $C_{2-6}$ alkenylcarbonyl, or arylalkenylcarbonyl which may be optionally substituted.

6. The compound according to claim 4, wherein $R^9$ represents a hydrogen atom and $R^{10}$ represents aryl.

7. The compound according to claim 6, wherein $R^3$ and $R^4$ represent a hydrogen atom.

8. The compound according to claim 4, wherein $R^4$ represents a hydroxyl group or aralkyloxy which may be optionally substituted.

9. The compound according to claim 1, wherein $R^1$ represents a hydroxyl group, $R^2$ represents —$CH_2OR^5$, $R^3$ represents $C_{1-6}$ alkyl and $R^4$ represents a hydroxyl group.

10. The compound according to claim 9, wherein $R^5$ represents a hydrogen atom.

11. A triterpene derivative represented by the formula (II) or a pharmaceutically acceptable salt thereof:

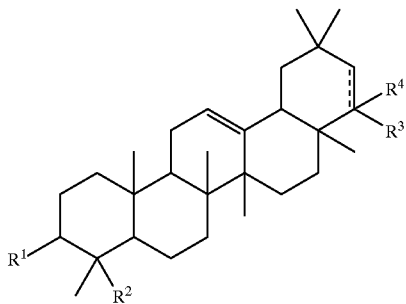

(II)

wherein $R^1$ represents a hydroxyl group;

$R^2$ represents —$CH_2OR^5$ wherein $R^5$ represents a hydrogen atom, $C_{1-6}$ alkyl, aralkyl which may be optionally substituted, or $C_{1-6}$ alkylcarbonyl;

$R^3$ represents a hydrogen atom; and $R^4$ represents $C_{1-6}$ alkyl,
hydroxy $C_{1-6}$ alkyl,
formyl,
—$COOR^{11}$ wherein $R^{11}$ represents a hydrogen atom or $C_{1-6}$ alkyl, or
—$OR^{12}$ wherein $R^{12}$ represents $C_{1-6}$ alkyl, aralkyl which may be optionally substituted, arylcarbonyl which may be optionally substituted, $C_{2-6}$ alkenyl, $C_{2-6}$ alkenylcarbonyl, or arylalkenylcarbonyl which may be optionally substituted.

12. The compound according to claim 11, wherein $R^5$ represents a hydrogen atom and $R^4$ represents —$OR^{12}$ wherein $R^{12}$ represents $C_{1-6}$ alkyl, aralkyl which may be optionally substituted, arylcarbonyl which may be optionally substituted, $C_{2-6}$ alkeenyl, $C_{2-6}$ alkenylcarbonyl, or arylalkenylcarbonyl which may be optionally substituted.

13. The compound according to claim 11, wherein $R^1$ represents a hydroxyl group, $R^2$ represents —$CH_2OR^5$, $R^3$ represents a hydrogen atom and $R^4$ represents hydroxy $C_{1-6}$ alkyl or —$COOR^{11}$.

14. The compound according to claim 13, wherein $R^5$ represents a hydrogen atom and $R^{11}$ represents a hydrogen atom.

15. A triterpene derivative represented by the formula (II) or a pharmaceutically acceptable salt thereof:

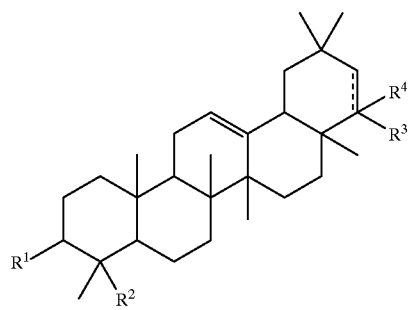

(II)

wherein $R^1$ represents aralkyloxy which may be optionally substituted, $R^2$ represents —$CH_2OR^5$, wherein $R^5$ represents a hydrogen atom, $C_{1-6}$ alkyl, or $C_{1-6}$ alkylcarbonyl, and $R^3$ and $R^4$ represent a hydrogen atom.

16. A triterpene derivative represented by the formula (II) or a pharmaceutically acceptable salt thereof:

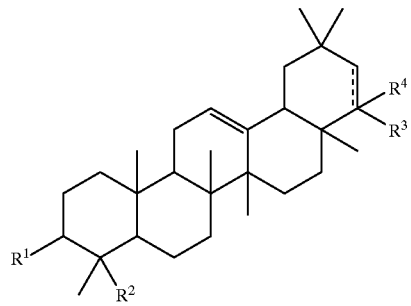

(II)

wherein $R^1$ represents a hydroxyl group, $R^2$ represents —$CH_2OR^5$, wherein $R^5$ represents $C_{1-6}$ alkyl or $C_{1-6}$ alkylcarbonyl, and $R^3$ and $R^4$ represent a hydrogen atom.

17. A triterpene derivative represented by the formula (II) or a pharmaceutically acceptable salt thereof:

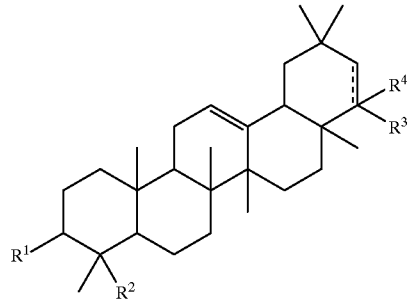

(II)

wherein $R^1$ represents a hydroxyl group, $C_{1-6}$ alkoxy, or $C_{1-6}$ alkylcarbonyloxy, $R^2$ represents —$CH_2OR^5$, wherein $R^5$ represents aralkyl which may be optionally substituted, and $R^3$ and $R^4$ represent a hydrogen atom.

18. A triterpene derivative represented by the formula (II) or a pharmaceutically acceptable salt thereof:

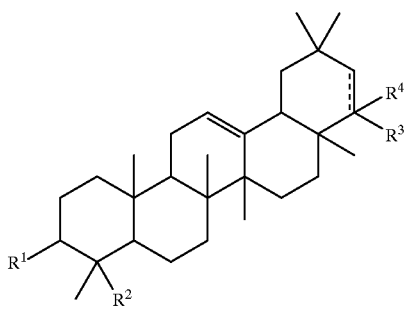

(II)

wherein $R^1$ represents $C_{1-6}$ alkoxy or $C_{1-6}$ alkylcarbonyloxy,
$R^2$ represents —$CH_2OH$ and $R^3$ and $R^4$ represent a hydrogen atom.

19. The compound according to claim 1, wherein $R^1$ represents a hydroxyl group, $R^2$ represents —$CH_2OR^5$ and $R^3$ and $R^4$ combine with each other to form a methylene group.

20. The compound according to claim 19, wherein $R^5$ represents a hydrogen atom.

21. The compound according to claim 1, wherein $R^1$ and $R^2$ combine with each other to form —O—$CR^9(R^{10})$—$OCH_2$— and ———— represents a double bond.

22. The compound according to claim 21, wherein $R^9$ and $R^{10}$ represent a methyl group.

23. A triterpene derivative represented by the formula (II) or a pharmaceutically acceptable salt thereof:

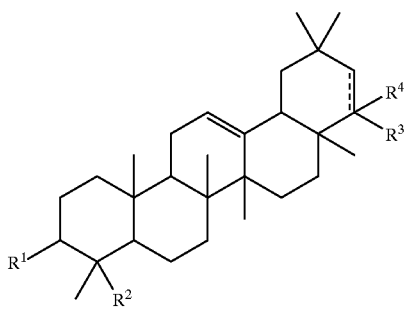

(II)

wherein in the formula (II), $R^1$ represents a hydroxyl group,
$R^2$ represents —COO—$C_{1-6}$ alkyl,
$R^3$ represents a hydrogen atom and
$R^4$ represents a hydroxyl group.

24. A triterpene derivative represented by the formula (II) or a pharmaceutically acceptable salt thereof:

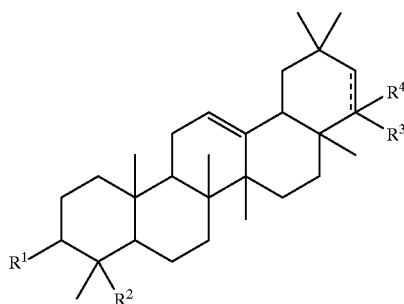

(II)

wherein in the formula (II), $R^1$ represents $C_{1-6}$ alkoxy,
$R^2$ represents —$CH_2OH$,
$R^3$ represents a hydrogen atom and
$R^4$ represents a hydroxyl group.

25. A triterpene derivative represented by the formula (II) or a pharmaceutically acceptable salt thereof:

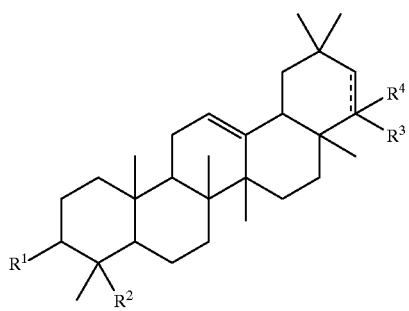

(II)

wherein in the formula (II), $R^1$ represents aralkyloxy,
$R^2$ represents formyl, carboxyl, —COO—$C_{1-6}$ alkyl or —$CH_2OR^5$, wherein $R^5$ represents a hydrogen atom, $C_{1-6}$ alkyl or $C_{1-6}$ alkylcarbonyl,
$R^3$ represents a hydrogen atom and
$R^4$ represents aralkyloxy.

26. A triterpene derivative represented by the formula (II) or a pharmaceutically acceptable salt thereof:

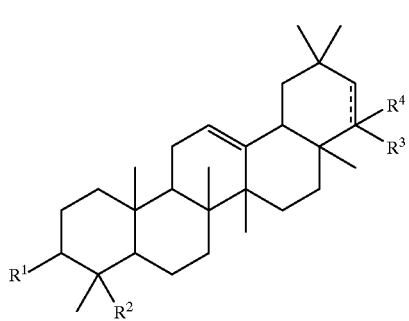

(II)

wherein in the formula (II), $R^1$ represents a hydroxyl group or $C_{1-6}$ alkoxy,
$R^2$ represents aralkyloxymethyl,
$R^3$ represents a hydrogen atom and
$R^4$ represents aralkyloxy.

27. The compound according to claim 1, which has a configuration represented by the following formula (II-1):

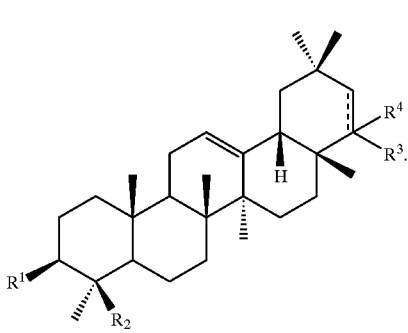

(II-1)

28. A method for treating a hepatic disorder excluding autoimmune hepatitis, comprising the step of administering to a mammal, including a human, a triterpene derivative represented by the formula (I) or a pharmaceutically acceptable salt thereof:

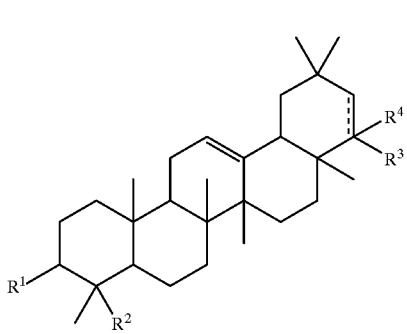

(I)

wherein
$R^1$ represents a hydroxyl group,
$C_{1-6}$ alkoxy,
$C_{1-6}$ alkylcarbonyloxy, or
aralkyloxy which may be optionally substituted;
$R^2$ represents $C_{1-6}$ alkyl,
—$CH_2OR^5$ wherein $R^5$ represents a hydrogen atom, $C_{1-6}$ alkyl, aralkyl which may be optionally substituted, or $C_{1-6}$ alkylcarbonyl,
formyl,
—$COOR^6$ wherein $R^6$ represents a hydrogen atom or $C_{1-6}$ alkyl), or
—$CH_2N(R^7)R^8$ wherein $R^7$ and $R^8$, which may be the same or different, represent a hydrogen atom or $C_{1-6}$ alkyl; or
$R^1$ and $R^2$ may combine with each other to form —O—$CR^9(R^{10})$—$OCH_2$— wherein $R^9$ and $R^{10}$, which may be the same or different, represent a hydrogen atom, $C_{1-6}$ alkyl, or aryl which may be optionally substituted;
$R^3$ and $R^4$, which may be the same or different, represent
a hydrogen atom,
a hydroxyl group,
$C_{1-6}$ alkyl,
hydroxy $C_{1-6}$ alkyl,
formyl,
—$COOR^{11}$ wherein $R^{11}$ represents a hydrogen atom or $C_{1-6}$ alkyl, or
—$OR^{12}$ wherein $R^{12}$ represents $C_{1-6}$ alkyl, aralkyl which may be optionally substituted, optionally substituted $C_{1-6}$ alkylcarbonyl, arylcarbonyl, $C_{2-6}$ alkenyl, $C_{2-6}$ alkenylcarbonyl, or arylalkenylcarbonyl which may be optionally substituted; or
$R^3$ and $R^4$ combine with each other to form a methylene group =O;

═ ─ ─ ─ represents a single or double bond, provided that, when ═ ─ ─ ─ represents a double bond, $R^4$ is absent.

29. The method for treating a hepatic disorder according to claim 28, wherein $R^1$ represents a hydroxyl group, $R^2$ represents —$CH_2OR^5$ and $R^3$ represents a hydrogen atom.

30. The method for treating a hepatic disorder according to claim 29, wherein $R^4$ represents a hydroxyl group or —$OR^{12}$.

31. The method for treating a hepatic disorder according to claim 28, wherein $R^1$ represents $C_{1-6}$ alkoxy.

32. The method for treating a hepatic disorder according to claim 28, wherein $R^1$ represents a hydroxyl group, $R^2$ represents formyl, $R^3$ represents a hydrogen atom and $R^4$ represents a hydroxyl group.

33. The method for treating a hepatic disorder according to claim 28, wherein $R^1$ represents a hydroxyl group or aralkyloxy which may be optionally substituted, $R^2$ represents —$COOR^6$, $R^3$ represents a hydrogen atom and $R^4$ represents a hydroxyl group or —$OR^{12}$.

34. The method for treating a hepatic disorder according to claim 28, wherein $R^1$ represents a hydroxyl group, $C_{1-6}$ alkoxy, $C_{1-6}$ alkylcarbonyloxy, $R^2$ represents —$CH_2OR^5$ and $R^3$ and $R^4$ represent a hydrogen atom.

35. The method for treating a hepatic disorder according to claim 28, wherein $R^1$ represents a hydroxyl group, $R^2$ represents —$CH_2OR^5$, $R^3$ represents $C_{1-6}$ alkyl and $R^4$ represents a hydroxyl group.

36. The method for treating a hepatic disorder according to claim 28, wherein $R^1$ represents a hydroxyl group, $R^2$ represents —$CH_2OR^5$, $R^3$ represents a hydrogen atom and $R^4$ represents hydroxy $C_{1-6}$ alkyl or carboxyl.

37. The method for treating a hepatic disorder according to claim 28, wherein the hepatic disorder is acute or chronic viral hepatitis, or drug-induced, toxic, alcoholic, intrahepatic cholestasis, or inborn metabolic error hepatopathy.

38. The method for treating a hepatic disorder according to claim 28, wherein the triterpene derivative represented by the formula (I) has a configuration represented by the following formula (I-1):

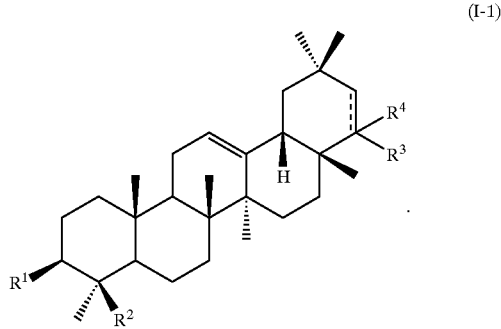

(I-1)

39. A pharmaceutical composition comprising the triterpene derivative or the pharmaceutically acceptable salt thereof according to claim 1.

40. 22β-Methoxyolean-12-ene-3β,24(4β)-diol or a pharmaceutically acceptable salt thereof.

41. 22β-Ethoxyolean-12-ene-3β,24(4β)-diol or a pharmaceutically acceptable salt thereof.

* * * * *